(12) United States Patent
Ashwell et al.

(10) Patent No.: US 8,614,228 B2
(45) Date of Patent: Dec. 24, 2013

(54) QUINONE PRODRUG COMPOSITIONS AND METHODS OF USE

(75) Inventors: Mark A. Ashwell, Carlisle, MA (US); Manish Tandon, Framingham, MA (US); Jean-Marc Lapierre, Pelham, NH (US); Yanbin Liu, Acton, MA (US)

(73) Assignee: ArQule, Inc., Woburn, MA (US)

( * ) Notice: Subject to any disclaimer, the term of this patent is extended or adjusted under 35 U.S.C. 154(b) by 1562 days.

(21) Appl. No.: 11/201,170

(22) Filed: Aug. 11, 2005

(65) Prior Publication Data

US 2006/0035963 A1    Feb. 16, 2006

Related U.S. Application Data

(60) Provisional application No. 60/600,373, filed on Aug. 11, 2004.

(51) Int. Cl.
*A01N 43/42* (2006.01)
*A61K 31/47* (2006.01)

(52) U.S. Cl.
USPC .......................................................... 514/310

(58) Field of Classification Search
USPC .................................................. 514/49, 310
See application file for complete search history.

(56) References Cited

U.S. PATENT DOCUMENTS

| | | | |
|---|---|---|---|
| 5,120,843 A | 6/1992 | McCall et al. | |
| 5,210,239 A | 5/1993 | Abe et al. | |
| 5,385,942 A | 1/1995 | Abe et al. | |
| 5,534,536 A * | 7/1996 | Ohuchida et al. | 514/397 |
| 5,674,900 A | 10/1997 | Ubillas et al. | |
| 5,763,625 A | 6/1998 | Boothman et al. | |
| 5,780,514 A | 7/1998 | Gutteridge et al. | |
| 5,783,598 A | 7/1998 | Boyd et al. | |
| 5,824,700 A | 10/1998 | Frydman et al. | |
| 5,840,900 A | 11/1998 | Greenwald et al. | |
| 5,880,131 A | 3/1999 | Greenwald et al. | |
| 5,969,163 A | 10/1999 | Frydman et al. | |
| 5,977,163 A | 11/1999 | Li et al. | |
| 6,245,807 B1 | 6/2001 | Pardee et al. | |
| 6,376,470 B1 | 4/2002 | Greenwald et al. | |
| 6,458,974 B1 | 10/2002 | Jiang et al. | |
| 6,608,076 B1 | 8/2003 | Greenwald et al. | |

(Continued)

FOREIGN PATENT DOCUMENTS

| | | |
|---|---|---|
| EP | 0040506 | 11/1981 |
| JP | 05124969 | 5/1993 |

(Continued)

OTHER PUBLICATIONS

Hooker (J. Am. Chem. Soc., 1936, 58 (7), 1190-1197).*

(Continued)

*Primary Examiner* — Benjamin Packard
(74) *Attorney, Agent, or Firm* — Mintz Levin Cohn Ferris Glovsky and Popeo, P.C.; Ivor R. Elrifi; Matthew Pavao

(57) ABSTRACT

The present invention relates to quinone prodrug compositions and therapeutic methods using such prodrug compositions. Preferably, the quinone compounds of the invention are napthoquinone compounds such as β-lapachone or β-lapachone analogs. The quinone prodrug compositions of the invention exhibit improved solubility, stability, bioavailability, and pharmacokinetic properties, as well as improved plasma half-life in vivo.

20 Claims, 1 Drawing Sheet

(56) References Cited

U.S. PATENT DOCUMENTS

| | | |
|---|---|---|
| 6,962,944 B2 | 11/2005 | Jiang et al. |
| 7,074,824 B2 | 7/2006 | Jiang et al. |
| 2002/0169135 A1 | 11/2002 | Pardee et al. |
| 2003/0091639 A1 | 5/2003 | Jiang et al. |
| 2004/0071775 A1 | 4/2004 | Jiang et al. |
| 2004/0087610 A1 | 5/2004 | Pardee et al. |
| 2004/0266857 A1 | 12/2004 | Jiang et al. |
| 2006/0034796 A1 | 2/2006 | Ashwell et al. |
| 2006/0035963 A1 | 2/2006 | Ashwell et al. |

FOREIGN PATENT DOCUMENTS

| | | |
|---|---|---|
| WO | WO 94/04145 | 3/1994 |
| WO | WO 95/05200 | 2/1995 |
| WO | WO-96/33988 A1 | 10/1996 |
| WO | WO 97/41093 | 11/1997 |
| WO | WO 00/61142 | 10/2000 |
| WO | WO 00/66175 | 11/2000 |
| WO | WO 00/66175 A3 | 11/2000 |
| WO | WO 01/26693 A2 | 4/2001 |
| WO | WO 01/70275 A2 | 9/2001 |
| WO | WO 02/058694 A2 | 8/2002 |
| WO | WO 03/011224 A2 | 2/2003 |
| WO | WO 03/011224 A2 | 2/2003 |
| WO | WO 03/053473 A2 | 7/2003 |
| WO | WO 03/090710 A1 | 11/2003 |
| WO | WO-2004/006849 A2 | 1/2004 |
| WO | WO 2004/045557 A2 | 6/2004 |
| WO | WO 2004/045557 A3 | 6/2004 |
| WO | WO 2005/082356 A2 | 9/2005 |
| WO | WO 2005/082357 A1 | 9/2005 |
| WO | WO-2006/020719 A2 | 2/2006 |
| WO | WO 2006/020722 A2 | 2/2006 |
| WO | WO-2006/128120 A2 | 11/2006 |

OTHER PUBLICATIONS

Bradshaw et al (Mol Cancer Ther. Feb. 2002;1(4):239-46).*

Ashraf et al., "Comparative Effects of Intraduodenal Psyllium and Senna on Canine Small Bowel Motility", *Aliment Pharmacol. Ther*, 8:329-336 (1994).

Bailey et al., "Involvement of DT-Diaphorase (EC 1.6.99.2) in the DNA Cross-Linking and Sequence Selectivity of the Bioreductive Anti-Tumour Agent EO9", *British Journal of Cancer*, 76(12):1596-1603 (1997).

Begleiter et al., "Induction of DT-Diaphorase in Cancer Chemoprevention and Chemotherapy", *Oncol. Res.*, 9:371-382 (1997).

Boorstein et al., "Coordinate Inhibition of DNA Synthesis and Thymidylate Synthase Activity Following DNA Damage and Repair", *Biochem. Biophys. Commun.*, 117(1):30-36 (1983).

Boothman et al., "Potentiation of Halogenated Pyrimidine Radiosensitizers in Human Carcinoma Cells by β-Lapachone (3,4-Dihydro-2,2-dimethyl-2H-naphtho[1,2-b]pyran-5,6-dione), a Novel DNA Repair Inhibitor", *Cancer Res.*, 47:5361-5366 (1987).

Choe et al., "Anticancer Drug Delivery Systems: $N^4$-Acyl Poly(Ethyleneglycol) Prodrugs of Ara-C. I. Efficacy in Solid Tumors", *Journal of Controlled Release*, 79:41-53 (2002).

Choe et al., "Anticancer Drug Delivery Systems: Multi-Loaded $N^4$-Acyl Poly(Ethylene Glycol) Prodrugs of Ara-C. II. Efficacy in Ascites and Solid Tumors", *Journal of Controlled Release*, 79:55-70 (2002).

Chuang et al., "Oxidative Free Radical Reaction of 2-Phenylthio-1,4-Naphthoquinones Initiated by Manganese(III)Manganese(II-I)Acetate", *Heterocycles*, 43(10):2215-2221 (1996).

Chung et al., "Acceleration of the Alcohol Oxidation Rate in Rats with Aloin, a Quinone Derivative of Aloe", *Biochem. Pharmacol.*, 52:1461-1468 (1996).

Clarys et al., "Efficacy of Topical Treatment of Pigmentation Skin Disorders with Plant Hydroquinone Glucosides as Assessed by Quantitative Color Analysis", *J. Dermatol.*, 25:412-414 (1998).

Conover et al., "Camptothecin Delivery Systems: Enhanced Efficacy and Tumor Accumulation of Camptothecin Following its Conjugation to Polyethylene Glycol via a Glycine Linker", *Cancer Chemother Pharmacol.*, 42(4):407-414 (1998).

Conover et al., "Camptothecin Delivery Systems: the Utility of Amino Acid Spacers for the Conjugation of Camptothecin with Polyethylene Glycol to Create Prodrugs", *Anticancer Drug Design*, 14(6):499-506 (1999).

Cortelli et al., "Clinical and Brain Bioenergetics Improvement with Idebenone in a Patient with Leber's Hereditary Optic Neuropathy: a Clinical and $^{31}$P-MRS Study", *J. Neurol. Sci.*, 148:25-31 (1997).

Driscoll et al. "Structure-Antitumor Activity Relationships Among Quinone Derivatives", *Cancer Chemot. Reports Part 2*, 4(2):1-362 (1974).

Duncan, Ruth, "The Dawning Era of Polymer Therapeutics", *Nature Reviews*, 2:347-360 (2003).

Etrych et al., "New HPMA Copolymers Containing Doxorubicin Bound Via pH-Sensitive Linkage: Synthesis and Preliminary In Vitro and In Vivo Biological Properties", *Journal of Controlled Release*, 73:89-102 (2001).

Etrych et al., "Synthesis of HPMA Copolymers Containing Doxorubicin Bound via a Hydrazone Linkage. Effect of Spacer on Drug Release and In Vitro Cytotoxicity", *Macromolecular Bioscience*, 2(1):43-52 (2002).

Frydman et al., "Induction of DNA Topoisomerase II-Mediated DNA Cleavage by β-Lapachone and Related Naphthoquinones", *Cancer Res.*, 57:620-627 (1997).

Gantchev et al., "Inhibition of the Topoisomerase II-DNA Cleavable Complex by the *ortho*-Quinone Derivative of the Antitumor Drug Etoposide (VP-16)", *Biochem. Biophys. Res. Comm.*, 237(1):24-27 (1997).

Gehrhardt et al., "Soluble Polymers in Organic Chemistry 5. Preparation of Carboxyl- and Amino-Terminal Polyethylene Glycol of Low Molecular Weight", *Polymer Bull.*, 18:487-493 (1987).

Gonalves et al., "Evaluation of the Toxicity of 3-Allyl-β-Lapachone Against *Trypa-Nosoma Cruzi* Bloodstream Forms", *Mol. Biochem. Parasitology*, 1:167-176 (1980).

Greenwald et al., "Drug Delivery System. 2. Camptothecin 20-*O*-Poly (Ethylene Glycol) Ester Transport Forms", *J. Med. Chem.*, 39(10):1938-1940 (1996).

Greenwald et al., "Drug Delivery Systems: Water Soluble Taxol 2'-Poly(ethylene glycol) Ester Prodrugs-Design and In Vivo Effectiveness", *J. Med. Chem.*, 39(2):424-431 (1996).

Greenwald et al., "Camptothecin-20-PEG Ester Transport Forms: the Effect of Spacer Groups on Antitumor Activity", *Bioorganic & Medicinal Chemistry*, 6:551-562 (1998).

Greenwald et al., "Drug Delivery Systems Employing 1,4- or 1,6-Elimination: Poly(Ethylene Glycol) Prodrugs of Amine-Containing Compounds", *J. Med. Chem.*, 42(18):3657-3667 (1999).

Greenwald et al., "Drug Delivery Systems Based on Trimethyl Lock Lactonization: Poly(Ethylene Glycol) Prodrugs of Amino-Containing Compounds", *J. Med. Chem.*, 43(3):475-487 (2000).

Greenwald et al., "Controlled Release of Proteins from Their Poly(ethylene Glycol) Conjugates: Drug Delivery Systems Employing 1,6-Elimination", *Bioconj. Chem.*, 14(2):395-403 (2003).

Greish et al., "Copoly(styrene-maleic acid)- Pirarubicin Micelles: High Tumor-Targeting Efficiency with Little Toxicity", *Bioconjugate Chem.*, 16(1):230-236 (2005).

Huang et al., "β-Lapachone Induces Cell Cycle Arrest and Apoptosis in Human Colon Cancer Cells" *Mol. Med.*, 5:711-720 (1999).

Krapcho et al., "Heterosubstituted Anthracene-9,10-dione Analogues. The Synthesis and Antitumor Evaluation of 5,8-Bis[(aminoalkyl)amino]Naphtho[2,3-b]Thiophene-4,9-diones", *J. Med. Chem.*, 33(9):2651-2655 (1990).

Krishnan et al., "Novel Mechanisms of DNA Topoisomerase II Inhibition by Pyranonaphthoquinone Derivatives-Eleutherin, α Lapachone, and β Lapachone", *Biochem Pharm*, 60:1367-1379 (2000).

Kurokawa, "The Reaction of Cadalene and Eudalene with Sulfur", *Bulletin of The Chemical Society of Japan*, 43(5):1454-1459 (1970).

Lai, et al., "β-Lapachone Induced Cell Death in Human Hepatoma (HepA2) Cells", *Histol Histopathol*, 13:89-97 (1998).

Li et al., "Induction of Apoptosis by β-Lapachone in Human Prostate Cancer Cells", *Cancer Res.*, 55:3712-3715 (1995).

(56) References Cited

OTHER PUBLICATIONS

Li et al., "β-Lapachone, a Novel DNA Topoisomerase I Inhibitor with a Mode of Action Different from Camptothecin", *J. Biol. Chem.*, 268(30):22463-22468 (1993).
Li et al., "Potent Inhibition of Tumor Survival in vivo by β-Lapachone Plus Taxol: Combining Drugs Imposes Different Artificial Checkpoints", *Proc. Natl. Acad. Sci. USA*, 96(23):13369-13374 (1999).
Li, "Release of Mitochondrial Cytochrome C in Both Apoptosis and Necrosis Induced by β-Lapachone in Human Carcinoma Cells", *Mol. Med.*, 5:232-239 (1999).
Li et al., "Potent Induction of Apoptosis by β-Lapachone in Human Multiple Myeloma Cell Lines and Patient Cells", *Mol. Med.*, 6(12):1008-1015 (2000).
Mahadik et al., "Oxidative Injury and Potential Use of Antioxidants in Schizophrenia", *Prostaglandins Leukot. Essent. Fatty Acids*, 55(1&2):45-54 (1996).
Matsumura et al., "A New Concept for Macromolecular Therapeutics in Cancer Chemotherapy: Mechanism of Tumoritropic Accumulation of Proteins and the Antitumor Agent Smancs", *Cancer Res.*, 46(12 Pt 1):6387-6392 (1986).
Mordente et al., "Antioxidant Properties of 2,3-Dimethoxy-5-methyl-6-(10-hydroxydecyl)-1,4-Benzoquinone (Idebenone)", *Chem. Res. Toxicol,*. 11:54-63 (1998).
Muller-Lissner, "Adverse Effects of Laxatives: Fact and Fiction", *Pharmacol.*, 47 (Suppl. 1):138-145 (1993).
Nanji et al., "Association Between Endothelial Cell Proliferation and Pathologic Changes in Experimental Alcoholic Liver Disease", *Toxicol. Appl. Pharmacol.*, 140:101-107 (1996).
Ochoa et al., *Proceedings of Am. Soc. of Clinical Oncology*, 19:(Abstract 770), (2000).
Pink et al., "NAD(P)H:Quinone Oxidoreductase Activity is the Principal Determinant of β-Lapachone Cytotoxicity" *J. Biol Chem.*, 275(8):5416-5424 (2000).
Planchon et al., "β-Lapachone-Mediated Apoptosis in Human Promyelocytic Leukemia (HL-60) and Human Prostate Cancer Cells: A p53-Independent Response", *Cancer Res.*, 55(17):3706-3711 (1995).
Portela et al., "Redox Cycling of β-Lapachone and Related o-Naphthoquinones in the Presence of Dihydrolipoamide and Oxygen", *Biochem Pharm*, 51:275-283 (1996).
Rao et al., "A Comparative Study of the Redox-Cycling of a Quinone (Rifamycin S) and a Quinonimine (Rifabutin) Antibiotic by Rat Liver Microsomes", *Free Radic. Biol. Med.*, 22(3):439-446 (1997).
Reinicke et al., "Development of β-Lapachone Prodrugs for Therapy Against Human Cancer Cells with Elevated NAD(P)H:Quinone Oxidoreductase 1 Levels", *Clin. Cancer. Res.*, 11(8):3055-64 (2005).
Rowinsky et al., "Phase I and Pharmacologic Study of High Doses of the Topoisomerase I Inhibitor Topotecan with Granulocyte Colony-Stimulating Factor in Patients with Solid Tumors", *Journal of Clinical Oncology*, 14(4):1224-1235 (1996).
Sartomer Website printed on May 24, 2006 (4 pages).
Singh et al., "Capsaicin (8-Methyl-N-Vanillyl-6-Nonenamide) Is a Potent Inhibitor of Nuclear Transcription Factor-κB Activation by Diverse Agents", *The Journal of Immunol.*, 157:4412-4420 (1996).
Suggs et al., "Facile Hydrolysis and Formation of Amide Bonds by N-Hydroxyethylation of α-Amino Acids", *Tetrahedron Letters*, 38(13):2227-2230 (1997).

Suginome et al., "One-Step Synthesis of 2,3-Dihydronaphtho[2,3-b]thiophene-4,9-diones by a New Regioselective [3+2] Photoaddition of Photogenerated 2-Mercapto-1,4-naphthoquinone with Alkenes", *J. Chem. Soc. Chem. Commun.*, 9:807-809 (1993).
Tapia et al., "Synthesis of 3,4-Dihydro-4-hydroxy-9-methoxy-2H-naphtho[2,3-b]thiopyranoquinone", *Tetrahedron Letters*, 38(1):153-154 (1997).
Tapia et al., "Synthesis of 2H-Naphtho[2,3-*b*]Thiopyranoquinones and Density Functional Study for the Diels-Alder Reaction of a Benzothiopyranoquinone", *Heterocycles*, 53(3):585-598 (2000).
Tonholo et al., "Electrochemical Properties of Biologically Active Heterocyclic Naphthoquinones", *J. Braz. Chem. Soc.*, 9(2):163-169 (1998).
Veronese et al., "Preparation, Physico-Chemical and Pharmacokinetic Characterization of Monomethoxypoly(Ethylene Glycol)-Derivatized Superoxide Dismutase", *Journal of Controlled Release*, 10:145-154 (1989).
Weller et al., "Topoisomerase-I Inhibitors for Human Malignant Glioma:Differential Modulation of p53, p21, bax and bcl-2 Expression and of CD95-Mediated Apoptosis by Camptothecin and β-Lapachone", *Int. J. Cancer*, 73: 707-714(1997).
Wuerzberger et al., "Induction of Apoptosis in MCF-7:WS8 Breast Cancer Cells by β-Lapachone", *Cancer Res.*, 58:1876-1885 (1998).
Yamaoka et al., "Distribution and Tissue Uptake of Poly(Ethylene Glycol) with Different Molecular Weights After Intravenous Administration to Mice", *Journal of Pharmaceutical Sciences*, 83(4):601-606 (1994).
Di Chenna et al., "Preparation and Cytotoxicity Toward Cancer Cells of Mono(arylimino) Derivatives of β-Lapachone", *Journal of Medicinal Chemistry*, 44:2486-2489 (2001).
International Search Report for International Application No. PCT/US2005/028445.
Kumi-Diaka et al., "Potential Mechanism of Phytochemical-induced Apoptosis in Human Prostate Adenocarcinoma Cells: Therapeutic Synergy in Genistein and β-Lapochone Combination Treatment", *Cancer Cell Treatment International*, 4:5 (2004).
Ohya et al., "Synthesis and Cytotoxic Activity of Conjugates of Monomethoxy-Poly(ethylene glycol) End-capped with Doxorubicin via Ester, Amide, or Schiff's Base Bond", *Journal of Bioactive and Compatible Polymers*, 10:51-66 (1995).
Partial International Search Results for PCT Application No. PCT/US2005/028438.
Powis et al., "Molecular Pharmacology and Antitumor Activity of Palmanunycin-based Inhibitors of Thioredoxin Reductase", *Molecular Cancer Therapeutics*, 5(3):630-636 (2006).
AI I . International Search Report for International Application No. PCT/US2005/028438.
Schaffner-Sabba et al., "β-Lapachone: Synthesis of Derivatives and Activities in Tumor Models", *J. Med. Chem.*, 27:990-994 (1984).
Pawliszyn, J., "Sampling and Sample Preparation for Field and Laboratory", Elsevier, p. 618 (2002).
Villar-Garea et al., "Procaine is a DNA-demethylating agent with growth-inhibitory effects in human cancer cells", *Cancer Res.*, 63:4984-4989 (2003).
Driscoll, J.S., "Quinone Structure-Antitumor Activity Relationships", *Cancer Chemother. Reports*, 4(4):3-4 (1974).
Li et al., "Selective killing of cancer cells by β-lapachone: Direct checkpoint activation as a strategy against cancer", *Proc. Natl. Acad. Sci. USA*. 100(5):2674-2678 (1993).

\* cited by examiner

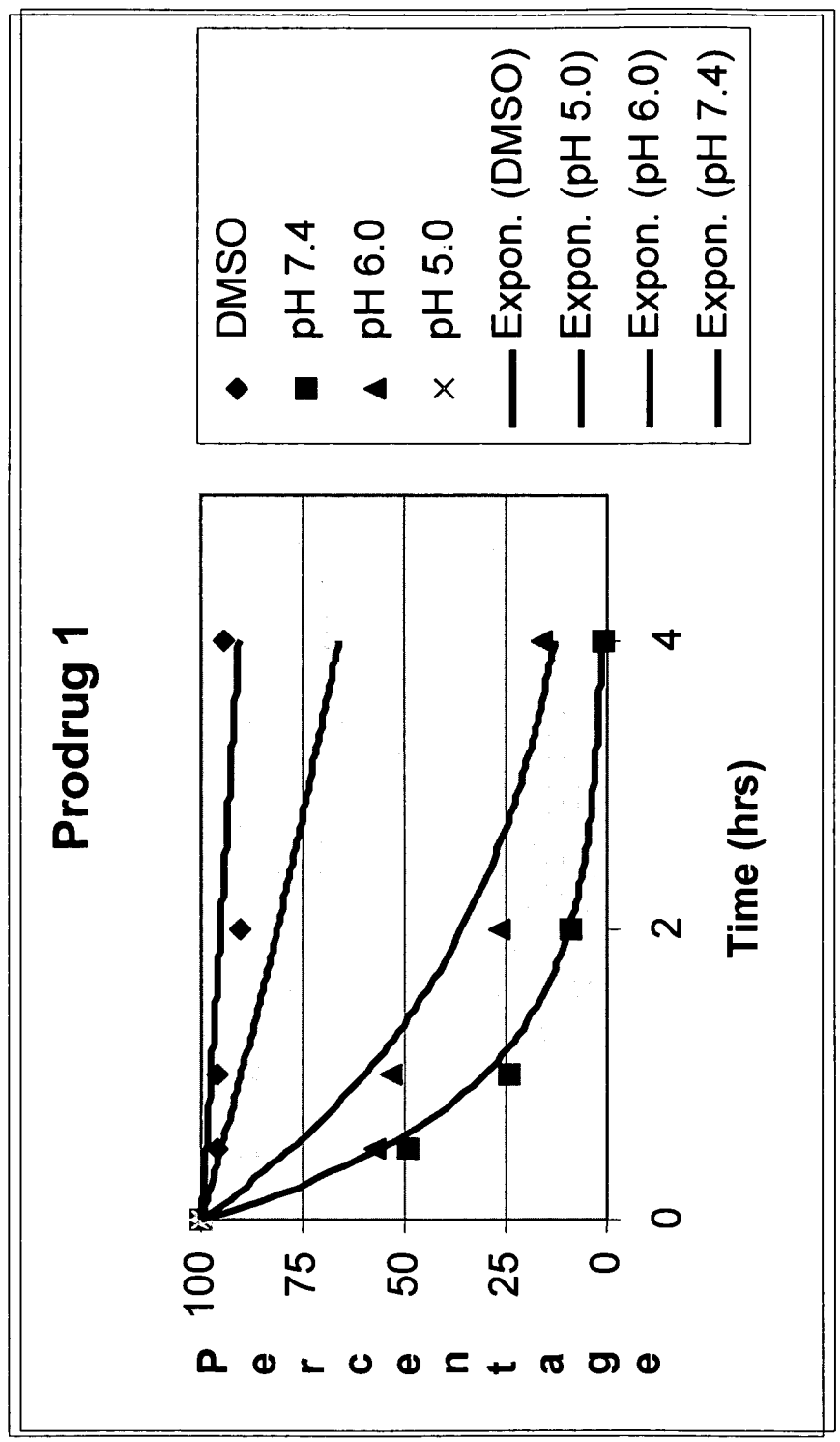

QUINONE PRODRUG COMPOSITIONS AND METHODS OF USE

RELATED APPLICATION

The present application claims the benefit of U.S. Provisional Application No. 60/600,373, filed Aug. 11, 2004, which application is herein incorporated by reference in its entirety. The present application also claims priority to PCT Application No. PCT/US2005/028438, filed Aug 11, 2005, which PCT application is herein incorporated by reference in its entirety.

FIELD OF THE INVENTION

The present invention relates to improved therapeutic agents and methods for treating cancer. More particularly, the invention relates to improved quinone and β-lapachone compositions and methods of using such compositions for the treatment of cancer.

BACKGROUND OF THE INVENTION

The quinones are a large and varied group of natural products found in all major groups of organisms. Quinones are a group of aromatic dioxo compounds derived from benzene or multiple-ring hydrocarbons such as naphthalene, anthracene, etc. They are classified as benzoquinones, naphthoquinones, anthraquinones, etc., on the basis of the ring system. Quinones have a variety of medicinal and industrial uses. Many efficient antineoplastic drugs are either quinones (anthracycline derivatives, mitoxantrone, actinomycin), quinonoid derivatives (quinolones, genistein, bactracyclin), or drugs such as etoposide that can easily be converted to quinones by in vivo oxidation. Gantchev et al. (1997) *Biochem. Biophys. Res. Comm.* 237:24-27. Quinones are now widely used as anticancer, antibacterial and anti-malarial drugs, as well as fungicides. The antitumor activities of the quinones were revealed more than two decades ago when the National Cancer Institute published a report in which fifteen-hundred synthetic and natural quinones were screened for their anticancer activities. Driscoll et al. (1974) *Cancer Chemot. Reports* 4:1-362.

More particularly, β-lapachone (3,4-dihydro-2,2-dimethyl-2H-naphtho[1,2-b]pyran-5,6-dione), a quinone, is derived from lapachol (a naphthoquinone) which can be isolated from the lapacho tree (Tabebuia avellanedae), a member of the catalpa family (Bignoniaceae). Lapachol and β-lapachone (with numbering) have the following chemical structures:

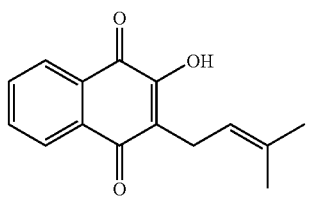

Lapachol

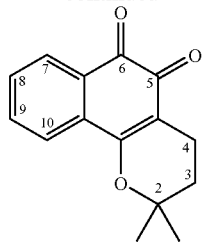

Beta-Lapachone

β-lapachone, as well as its intermediates, derivatives and analogs thereof, are described in Li, C. J. et al., (1993) *J. Biol. Chem.*, 268(30): 22463-22468.

As a single agent, β-lapachone has demonstrated significant antineoplastic activity against human cancer cell lines at concentrations typically in the range of 1-10 μM ($IC_{50}$). Cytotoxicity has been demonstrated in transformed cell lines derived from patients with promyelocytic leukemia (Planchon et al., (1996) *Cancer Res.*, 55: 3706-3711), prostate (Li, C. J., et al., (1995) *Cancer Res.*, 55: 3712-3715), malignant glioma (Weller, M. et al., (1997) *Int. J. Cancer*, 73: 707-714), hepatoma (Lai, C. C., et al., (1998) *Histol Histopathol*, 13: 89-97), colon (Huang, L., et al., (1999) *Mol Med*, 5: 711-720), breast (Wuertzberger, S. M., et al., (1998) *Cancer Res.*, 58: 1876), ovarian (Li, C. J. et al., (1999) *Proc. Natl. Acad. Sci. USA*, 96(23): 13369-13374), pancreatic (Li, Y., et al., (2000) *Mol Med*, 6: 1008-1015; Li, Y., (1999) *Mol Med*, 5: 232-239), and multiple myeloma cell lines, including drug-resistant lines (Li, Y., (2000) *Mol Med*, 6: 1008-1015). No cytotoxic effects were observed on normal fresh or proliferating human PBMC (Li, Y., (2000) *Mol Med*, 6: 1008-1015).

β-lapachone appears to work by inducing unscheduled expression of checkpoint molecules, e.g., E2F, independent of DNA damage and cell cycle stages. Several studies have shown that β-lapachone activates checkpoints and induces apoptosis in cancer cells from a variety of tissues without affecting normal cells from these tissues (U.S. Patent Application Publication No. 2002/0169135, incorporated by reference herein). In normal cells with their intact regulatory mechanisms, such an imposed expression of a checkpoint molecule results in a transient expression pattern and causes little consequence. In contrast, cancer and pre-cancer cells have defective mechanisms, which result in unchecked and persistent expression of unscheduled checkpoint molecules, e.g., E2F, leading to selective cell death in cancer and pre-cancer cells.

β-lapachone has been shown to be a DNA repair inhibitor that sensitizes cells to DNA-damaging agents including radiation (Boothman, D. A. et al., *Cancer Res*, 47 (1987) 5361; Boorstein, R. J., et al., *Biochem. Biophys. Commun.*, 117 (1983) 30). β-lapachone has also shown potent in vitro inhibition of human DNA Topoisomerases I (Li, C. J. et al., *J. Biol. Chem.*, 268 (1993) 22463) and II (Frydman, B. et al., *Cancer Res.*, 57 (1997) 620) with novel mechanisms of action. Unlike topoisomerase "poisons" (e.g., camptothecin, etoposide, doxorubicin) which stabilize the covalent topoisomerase-DNA complex and induce topoisomerase-mediated DNA cleavage, β-lapachone interacts directly with the enzyme to inhibit catalysis and block the formation of cleavable complex (Li, C. J. et al., *J. Biol. Chem.*, 268 (1993) 22463) or with the complex itself, causing religation of DNA breaks and dissociation of the enzyme from DNA (Krishnan, P. et al., *Biochem Pharm*, 60 (2000) 1367). β-lapachone and its derivatives have also been synthesized and tested as antiviral and anti-parasitic agents (Goncalves, A. M., et al., *Mol. Biochem. Parasitology*, 1 (1980) 167-176; Schaffner-Sabba, K., et al., *J. Med. Chem.*, 27 (1984) 990-994).

More specifically, β-lapachone appears to work by disrupting DNA replication, causing cell-cycle delays in G1 and/or S phase, inducing either apoptotic or necrotic cell death in a wide variety of human carcinoma cell lines without DNA damage and independent of p53 status (Li, Y. Z. et al. (1999); Huang, L. et al.). Topoisomerase I is an enzyme that unwinds the DNA that makes up the chromosomes. The chromosomes must be unwound in order for the cell to use the genetic information to synthesize proteins; β-lapachone keeps the chromosomes wound tight, so that the cell cannot make proteins. As a result, the cell stops growing. Because cancer cells are constantly replicating and circumvent many mechanisms that restrict replication in normal cells, they are more vulnerable to topoisomerase inhibition than are normal cells.

Another possible intracellular target for β-lapachone in tumor cells is the enzyme NAP(P)H:quinone oxidoreductase (NQO1). Biochemical studies suggest that reduction of β-lapachone by NQO1 leads to a "futile cycling" between the quinone and hydroquinone forms with a concomitant loss of reduced NADH or NAD(P)H (Pink, J. J. et al., *J. Biol. Chem.*, 275 (2000) 5416). The exhaustion of these reduced enzyme cofactors may be a critical factor for the activation of the apoptotic pathway after β-lapachone treatment.

As a result of these findings, β-lapachone is actively being developed for the treatment of cancer and tumors. In WO 00/61142, for example, there is disclosed a method and composition for the treatment of cancer, which comprises the administration of an effective amount of a first compound, a $G_1$ or S phase drug, such as a β-lapachone, in combination with a $G_2$/M drug, such as a taxane derivative. Additionally, U.S. Pat. No. 6,245,807 discloses the use of β-lapachone, amongst other β-lapachone derivatives, for use in the treatment of human prostate disease.

In addition to β-lapachone, a number of β-lapachone analogs having anti-proliferative properties have been disclosed in the art, such as those described in PCT International Application PCT/US93/07878 (WO 94/04145), which is incorporated by reference herein, and U.S. Pat. No. 6,245,807, incorporated by reference herein, in which a variety of substituents may be attached at positions 3- and 4- on the β-lapachone compound. PCT International Application PCT/US00/10169 (WO 00/61142), incorporated by reference herein, discloses β-lapachone, which may have a variety of substituents at the 3-position as well as in place of the methyl groups attached at the 2-position. U.S. Pat. Nos. 5,763,625, 5,824,700, and 5,969,163, each of which is incorporated by reference herein, disclose analogs with a variety of substituents at the 2-, 3- and 4-positions. Furthermore, a number of journals report β-lapachone analogs with substituents at one or more of the following positions: 2-, 3-, 8- and/or 9-positions, (See, Sabba et al., (1984) *J Med Chem* 27:990-994 (substituents at the 2-, 8- and 9-positions); (Portela and Stoppani, (1996) *Biochem Pharm* 51:275-283 (substituents at the 2- and 9-positions); Goncalves et al., (1998) *Molecular and Biochemical Parasitology* 1:167-176 (substituents at the 2- and 3-positions)).

Moreover, structures having sulfur-containing hetero-rings in the "α" and "β" positions of lapachone have been reported (Kurokawa S, (1970) *Bulletin of The Chemical Society of Japan* 43:1454-1459; Tapia, R A et al., (2000) *Heterocycles* 53(3):585-598; Tapia, R A et al., (1997) *Tetrahedron Letters* 38(1):153-154; Chuang, C P et al., (1996) *Heterocycles* 40(10):2215-2221; Suginome H et al., (1993) *Journal of the Chemical Society, Chemical Communications* 9:807-809; Tonholo J et al., (1988) *Journal of the Brazilian Chemical Society* 9(2):163-169; and Krapcho A P et al., (1990) *Journal of Medicinal Chemistry* 33(9):2651-2655). More particularly, hetero β-lapachone analogs are disclosed in PCT International Application PCT/US03/037219 (WO 04/045557), incorporated by reference herein.

Quinones also have a number of other medicinal uses. Terpenoid-type quinones are also useful as treatments for diabetes. U.S. Pat. No. 5,674,900. Additional quinones can be used to treat cirrhosis and other liver disorders. U.S. Pat. Nos. 5,210,239 and 5,385,942.

Hydroquinone amines and quinone amines are also useful for treating a number of conditions, including spinal trauma and head injury. U.S. Pat. No. 5,120,843. Degenerative central nervous system diseases, as well as vascular diseases, are treatable with quinones such as Idebenone [2,3-dimethoxy-5-methyl-6-(10-hydroxydecyl)-1,4-benzoquinone] and Rifamycin. S. Mordente et al. (1998) *Chem. Res. Toxicol.* 11:54-63; Rao et al. (1997) *Free Radic. Biol. Med* 22:439-46; Cortelli et al. (1997) *J. Neurol. Sci.* 148:25-31; and Mahadik et al. (1996) *Prostaglandins Leukot. Essent. Fatty Acids* 55:45-54. A vitamin K analog, 6-cyclo-octylamino-5,8-quinoline quinone shows efficacy for treatment of leprosy and tuberculosis. U.S. Pat. No. 4,963,565. Hydroquinone is also used to treat skin pigmentation disorders. Clarys et al. (1998) *J. Dermatol.* 25:412-4. Mitomycin C-related drug indoloquinone EO9 has demonstrated cell killing against HL-60 human leukemia cells, H661 human lung cancer cells, rat Walker tumor cells and human HT29 colon carcinoma cells. Begleiter et al. (1997) *Oncol. Res.* 9:371-82; and Bailey et al. (1997) *Br. J. Cancer* 76:1596-603.

Quinones such as aloin, a C-glycoside derivative of anthraquinone, accelerate ethanol oxidation and may be useful in treating acute alcohol intoxication. Chung et al. (1996) *Biochem. Pharmacol.* 52:1461-8 and Nanji et al. (1996) *Toxicol. Appl. Pharmacol.* 140:101-7. Quinones capsaicin and resiniferatoxin blocked activation of nuclear transcription factor NF-κB, which is required for viral replication, immune regulation and induction of various inflammatory and growth-regulatory genes. Singh et al. (1996) *J. Immunol.* 157:4412-20. Antiretroviral and antiprotozoan naphthoquinones are described in U.S. Pat. Nos. 5,780,514 and 5,783, 598. Anthraquinones are also useful as laxatives. Ashraf et al. (1994) *Aliment. Pharmacol. Ther.* 8:329-36; and Muller-Lissner (1993) *Pharmacol.* 47 (Suppl. 1): 138-45.

Because of the wide variety of biological processes in which quinones play a critical role, it would be advantageous to develop novel quinones for various uses, including disease treatment.

One obstacle, however, to the development of pharmaceutical formulations comprising quinones, such as β-lapachone or β-lapachone analogs for pharmaceutical use is the low solubility of many quinone compounds, including β-lapachone compounds, in pharmaceutically acceptable solvents. There are also drawbacks related to the pharmacokinetic profiles of traditional formulations comprising quinones. As a result, there is a need for improved formulations of quinone compounds for pharmaceutical administration, which are both safe and readily bioavailable to the subject to which the formulation is administered.

SUMMARY OF THE INVENTION

The present invention relates generally to quinone prodrug compositions comprising a quinone compound covalently linked to one or two pro-moieties, such as an amino acid moiety or other water solubilizing moiety. The quinone compound may be released from the pro-moiety via hydrolytic, oxidative, and/or enzymatic release mechanisms.

The quinone prodrug compositions of the invention exhibit the added benefit of increased aqueous solubility, improved stability, and improved pharmacokinetic profiles. The pro-moiety may be selected to obtain desired prodrug characteristics. For example, the pro-moiety, e.g., an amino acid moiety or other water solubilizing moiety, may be selected based on solubility, stability, bioavailability, and/or in vivo delivery or uptake.

In a preferred embodiment, the pro-moiety may be attached at either or both of the quinone carbonyls. If a single pro-moiety is attached to the quinone compound, the uncomplexed quinone carbonyl group may independently be linked to a desired moiety to obtain desired properties. For instance, the uncomplexed quinone carbonyl may be substituted with a bioactive moiety to enhance the bioactivity of the quinone compound, or to confer an additional bioactivity to the quinone prodrug composition.

Preferred pro-moieties include amino acid moieties, such as amino acid residues, proteins and peptides; and carboxylic acids, such as malonic acid, succinic acid, and nicotinic acid.

In another aspect, the present invention relates to therapeutic methods using the quinone prodrug compositions of the invention. The methods of the invention can by used to treat or prevent any disease or condition in which the quinone compound is useful. In particular, the methods of the invention relate to the treatment of cancer.

In yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form.

These and other aspects of the invention are discussed in further detail below.

Certain Embodiments

1. A quinone prodrug composition comprising a quinone compound covalently attached to one or two independently selected pro-moieties, to thereby form the quinone prodrug composition.

2. The quinone prodrug composition of embodiment 1, wherein the quinone compound is covalently attached to one pro-moiety, and wherein either one or both regioisomer is formed.

3. The quinone prodrug composition of embodiment 1, wherein at least one of the one or two independently selected pro-moieties is an amino acid moiety or other water-solubilizing moiety.

4. The quinone prodrug composition of embodiment 1, wherein at least one of the one or two independently selected pro-moieties is an amino acid moiety.

5. The quinone prodrug composition of embodiment 4, wherein the amino acid moiety is a natural or unnatural amino acid residue.

6. The quinone prodrug composition of embodiment 5, wherein the amino acid residue is selected from the group consisting of glycine, alanine, valine, and proline.

7. The quinone prodrug composition of embodiment 4, wherein the amino acid moiety is a peptide or protein.

8. The quinone prodrug composition of embodiment 1, wherein at least one of the one or two independently selected pro-moieties is a carboxylic acid.

9. The quinone prodrug composition of embodiment 8, wherein the carboxylic acid is selected from the group consisting of malonic acid, succinic acid, and nicotinic acid.

10. The quinone prodrug composition of embodiment 1, wherein the quinone compound is a 1,2-napthoquinone.

11. The quinone prodrug composition of embodiment 1, wherein the quinone compound is β-lapachone or analog thereof.

12. The quinone prodrug composition of embodiment 1, wherein the quinone compound is β-lapachone.

13. The quinone prodrug composition of embodiment 1, wherein the composition is a compound of Formula 1a.

14. The quinone prodrug composition of embodiment 1, wherein the composition is a compound selected from the group consisting of Prodrug 1 to Prodrug 28.

15. The quinone prodrug composition of embodiment 1, wherein the quinone compound is a β-lapachone analog which comprises at least one hydrogen substituted for a methyl group at the 2 position of β-lapachone.

16. The quinone prodrug composition of embodiment 1, wherein the quinone compound is a β-lapachone analog which comprises a hydroxy group or a $C_1$ to $C_4$ alkyl group optionally substituted with a hydroxy group, substituted for a hydrogen at the 3 or 4 position of β-lapachone.

17. The quinone prodrug composition of embodiment 1, wherein the quinone compound is a β-lapachone analog which comprises a heteroatom selected from the group consisting of oxygen, nitrogen, and sulfur, substituted for the ring atom at the 1, 2, 3, or 4 position of β-lapachone.

18. A pharmaceutical composition comprising a therapeutically effective amount of at least one quinone prodrug composition and a pharmaceutically acceptable excipient, wherein said quinone prodrug composition comprises a quinone compound covalently linked to one or two amino acid moieties.

19. The pharmaceutical composition of embodiment 18, wherein the at least one quinone prodrug composition is a prodrug composition of any of embodiments 1-17.

20. The pharmaceutical composition of embodiment 18, wherein the pharmaceutical composition is an aqueous solution.

21. The pharmaceutical composition of embodiment 18, wherein the pharmaceutical composition is a lyophilized solid.

22. The pharmaceutical composition of embodiment 18, wherein the pharmaceutical composition comprises 0.1 mg/ml to 10 mg/ml of the quinone prodrug composition.

23. The pharmaceutical composition of embodiment 18, further comprising a second anticancer agent.

24. The pharmaceutical composition of embodiments 23, wherein the second anticancer agent is selected from the group consisting of taxane derivatives, gemcitabine, other nucleoside and nucleotide anticancer agents, cisplatin, imatnibmeasylate, and trastuzumab.

25. The pharmaceutical composition of embodiment 24, wherein the taxane derivative is paclitaxel or docetaxol.

26. A method for treating cancer in a subject comprising administering a quinone prodrug composition of any of embodiments 1-17 to a subject in need thereof.

27. A method for treating cancer in a subject comprising administering a pharmaceutical composition comprising a quinone prodrug composition of any of embodiments 18-25 to a subject in need thereof.

28. The method of embodiment 26, wherein the pharmaceutical composition is administered parenterally.

29. The method of embodiment 26, wherein the pharmaceutical composition is administered orally.

30. The method of embodiment 26, wherein between 0.1 mg/kg to 10 mg/kg of the quinone prodrug composition is administered from between twice weekly to once every four weeks.

31. The method of embodiment 26, wherein the method comprises administering a second anticancer agent to the subject.

32. The method of embodiment 31, wherein the second anticancer agent is selected from the group consisting of taxane derivatives, gemcitabine, other nucleoside and nucleotide anticancer agents, cisplatin, imatnibmeasylate, and trastuzumab.

33. The method of embodiment 32, wherein the taxane derivative is paclitaxel or docetaxol.

34. The method of any of embodiments 31-33, wherein the second anticancer agent is administered simultaneously with or sequentially to the quinone prodrug composition.

35. The method of embodiment 27, wherein the pharmaceutical composition comprises a second anticancer agent.

36. The method of any of embodiments 26-35, wherein the cancer is characterized by the presence of one or more solid tumors.

37. The method of any of embodiments 26-35, wherein the cancer is prostate cancer.

38. The method of any of embodiments 26-35, wherein the cancer is multiple myeloma.

39. The method of any of embodiments 26-35, wherein the cancer is a hematologic tumor.

40. The method of any of embodiments 26-35, wherein the cancer is a lymphoid tumor.

41. The method of any of embodiments 26-35, wherein the cancer is ovarian cancer.

42. The method of any of embodiments 26-35, wherein the cancer is breast cancer.

43. A kit for the treatment of a mammalian cancer comprising at least one vial containing a quinone prodrug composition of any of embodiments 1-17.

44. A kit of embodiment 43, wherein the kit further comprises, within in the same vial or a separate vial, a second anticancer agent.

45. The kit of embodiment 44, wherein the second anticancer agent is is selected from the group consisting of taxane derivatives, gemcitabine, other nucleoside and nucleotide anticancer agents, cisplatin, imatnibmeasylate, and trastuzumab.

46. The kit of embodiment 45, wherein the taxane derivative is paclitaxel or docetaxol.

BRIEF DESCRIPTION OF THE DRAWINGS

FIG. 1 illustrates the release of β-lapachone form a preferred a β-lapachone prodrug composition of the invention.

DETAILED DESCRIPTION OF THE INVENTION

The present invention relates generally to quinone prodrug compositions comprising a quinone compound covalently linked to one or two pro-moieties, such as an amino acid moiety or other water solubilizing moiety, to thereby result in a quinone prodrug composition. The quinone compound may be released from the pro-moiety via hydrolytic, oxidative, and/or enzymatic release mechanisms.

The quinone prodrug compositions of the invention exhibit the added benefit of increased aqueous solubility, improved stability, and improved pharmacokinetic profiles. The pro-moiety may be selected to obtain desired prodrug characteristics. For example, the pro-moiety, e.g., an amino acid moiety, may be selected based on solubility, stability, bioavailability, and/or in vivo delivery or uptake.

A. Quinone and β-Lapachone Compounds of the Invention

The prodrug compositions of the present invention comprise a quinone compound. The quinone compound is preferably a napthoquinone compound, more preferably a 1,2-napthoquinone compound, including β-lapachone and analogs thereof.

Preferred β-lapachone compounds of the invention include β-lapachone and analogs thereof. As discussed above, β-lapachone has the following chemical structure (Compound 1, with numbering):

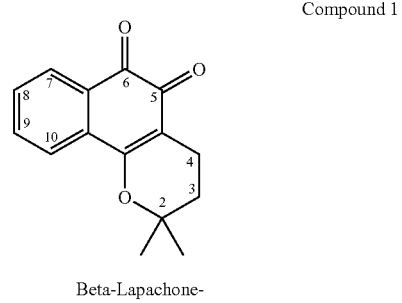 [SMILES: CC1(C)CCC2=C(O1)c1ccccc1C(=O)C2=O]

Compound 1

Beta-Lapachone-

β-lapachone analogs include compounds that are structural derivatives of β-lapachone, differing from β-lapachone by substitution of one, two, three, four, or more elements of β-lapachone with a different group or element. For example, a hydrogen at the 3 or 4 position may be substituted with a hydroxy or a $C_1$-$C_4$ alkyl, wherein the $C_1$-$C_4$ alkyl is optionally substituted with a hydroxy. Preferred substituents include 3-hydroxy and 3-methanolyl. Further, each of the methyl groups at position 2 may be independently substituted with a hydrogen. The β-lapachone analogs of the invention may also include substitutions of heteroatoms, for instance, the oxygen at position I may be substituted with a sulfur atom, and the carbon at position 4 may be substituted with an oxygen.

Any β-lapachone analog known in the art may be used as the β-lapachone compound of the invention. For instance, a number of β-lapachone analogs having anti-proliferative properties have been disclosed in the art, such as those described in PCT International Application PCT/US93/07878 (WO 94/04145), which is incorporated by reference herein, and U.S. Pat. No. 6,245,807, incorporated by reference herein, in which a variety of substituents may be attached at positions 3- and 4- on the β-lapachone compound. PCT International Application PCT/US00/10169 (WO 00/61142), incorporated by reference herein, discloses β-lapachone, which may have a variety of substituents at the 3-position as well as in place of the methyl groups attached at the 2-position. U.S. Pat. Nos. 5,763,625, 5,824,700, and 5,969,163, each of which is incorporated by reference herein, disclose analogs with a variety of substituents at the 2-, 3- and 4-positions. Furthermore, a number of journals report β-lapachone analogs with substituents at one or more of the following positions: 2-, 3-, 8- and 9-positions, See, e.g., Sabba et al., (1984) *J Med Chem* 27:990-994 (substituents at the 2-, 8- and 9-positions); Portela and Stoppani, (1996) *Biochem Pharm* 51:275-283 (substituents at the 2- and 9-positions); Goncalves et al., (1998) *Molecular and Biochemical Parasitology* 1:167-176 (substituents at the 2- and 3-positions).

Moreover, structures having sulfur-containing heterorings in the "α" and "β" positions of lapachone have been reported (Kurokawa S, (1970) *Bulletin of The Chemical Society of Japan* 43:1454-1459; Tapia, R A et al., (2000) *Heterocycles* 53(3):585-598; Tapia, R A et al., (1997) *Tetrahedron Letters* 38(1):153-154; Chuang, C P et al., (1996) *Heterocycles* 40(10):2215-2221; Suginome H et al., (1993) *Journal of the Chemical Society, Chemical Communications* 9:807-809; Tonholo J et al., (1988) *Journal of the Brazilian Chemical Society* 9(2):163-169; and Krapcho A P et al., (1990) *Journal of Medicinal Chemistry* 33(9):2651-2655). More particularly, hetero β-lapachone analogs are disclosed in PCT International Application PCT/US03/037219 (WO 04/045557), incorporated by reference herein.

B. Pro-Moieties of the Invention

The pro-moiety of the invention may be selected so as to obtain desired solubility, stability, bioavailability, pharmacokinetic properties, or targeted/selective in vivo drug delivery. The pro-moiety may be covalently attached to either or both of the quinone carbonyl groups.

The pro-moiety is preferably an amino acid moiety or other water solubilizing moiety. An amino acid moiety useful in the present invention may be any natural or unnatural amino acid residue, or a desired protein or peptide. Peptide pro-moieties include peptides that may be covalently bound by an amine or carboxyl group of the peptide or by a carboxamide group formed by an amino group bonded to the carboxyl terminal COOH group of the peptide chain. Other preferred water solubilizing moieties include carboxylic acids such as for example malonic acid, succinic acid, and nicotinic acid. Pro-moieties of the present invention also include the side chain of a naturally occurring alpha amino acid or in an alternative embodiment the side chain, alpha carbon, and the alpha amino group of a naturally occurring amino acid (e.g., an alpha amino acid without its carboxyl group).

Naturally occurring alpha amino acids include alanine, valine, leucine, isoleucine, phenylalanine, tryptophan, methionine, glycine, serine, threonine, cysteine, tyrosine, asparagine, glutamine, aspartic acid, glutamic acid, lysine, arginine, proline, and histidine. Preferred amino acid residues include glycine, alanine, valine and proline. Preferred protein or peptide moieties may be selected to obtain desired targeted/selective in vivo drug delivery.

In another embodiment, pro-moieties of the present invention include aryl or heteroaryl groups, either of which may be optionally substituted with a ($C_1$-$C_6$) alkyl group, an aryl group, or a heteroaryl group. In another embodiment, a pro-moiety of the present invention is an aryl group optionally substituted with a heteroaryl group. In a further embodiment, a pro-moiety of the present invention is a heteroaryl group optionally substituted with an alkyl group. In an embodiment, pro-moieties of the present invention include: —COOH, —$CH_2$—COOH, —$(CH_2)_2$COOH, 1-pyridyl, 2-pyridyl, 3-pyridyl, 4-pyridyl, aryl, alkyl-aryl, heteroaryl, alkyl-heteroaryl, aryl-heteroaryl, alkyl-aryl-heteroaryl,

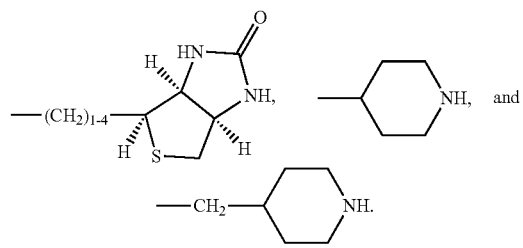

Exemplary aryl and heteroaryl containing pro-moieties include without limitation —($C_0$-$C_6$)alkyl-aryl, and —($C_0$-$C_6$)alkyl-aryl-heteroaryl, —($C_0$-$C_6$)alkyl-heteroaryl. Aryl and heteroaryl rings present in pro-moieties, including pyridyl, phenyl, imidazole, and thiazole rings, may be substituted with one or more independently selected ($C_1$-$C_3$) alkyl groups.

C. Quinone Prodrug Compositions and β-Lapachone Prodrug Compositions

As discussed above, the quinone prodrug compositions of the invention generally comprise a quinone compound covalently attached to one or two pro-moieties, such as an amino acid moiety or other water solubilizing moiety. In a preferred embodiment, the pro-moiety may be attached at either or both of the quinone carbonyls. If a single pro-moiety is attached to the quinone compound, the uncomplexed quinone carbonyl group may independently be linked to a desired moiety to obtain desired properties. For instance, the uncomplexed quinone carbonyl may be substituted with a bioactive moiety to enhance the bioactivity of the quinone compound, or to confer an additional bioactivity to the quinone prodrug composition.

By way of example, preferred β-lapachone prodrug compositions are illustrated below in Formula I. However, it is understood that similar pro-moiety substitutions can be made to any quinone compound of the invention, including any napthoquinone compound such as for example 1,2-napthoquinone compounds. Regioisomer ratios can vary, with the predominant isomer illustrated in Formula I. However, the opposite isomer is also within the scope of the invention.

Formula I

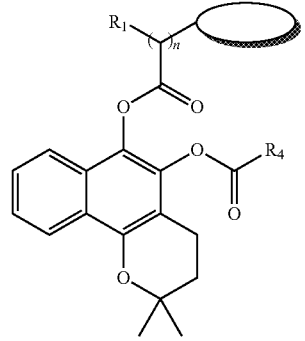

$R_1$ is independently selected from H; or alkyl, optionally substituted with a sulfyl (—SH or thio alkyl) group;

$R_4$ is independently alkyl, aromatic, or can be a pro-moiety, or form part of the pro-moiety of the 1-carbonyl;

n is 0, 1, 2, or 3, with the proviso that when n is 0, $R_1$ is not present.

In a further embodiment, $R_1$ is a ($C_1$-$C_4$) alcohol and $R_4$ and n are as described above.

In an embodiment, where n=0 and $R_1$ is not present, β-lapachone prodrug compositions are of the form:

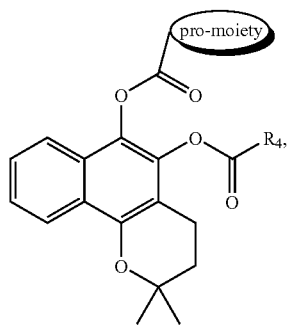

wherein the carboxyl pro-moiety group, identified as

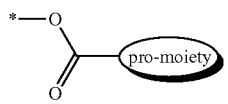 [SMILES: *OC(C)=O]

(where * indicates the point of attachment to beta-lapachone) is selected from the group consisting of: a peptide, a peptide bearing one or more N-methyl groups, a peptide bearing one or more N-ethyl groups, an amino acid, and a carboxylic acid; and $R_4$ is as defined above.

Where the carboxyl pro-moiety group is a peptide, it may be attached to a quinone compound (e.g., β-lapachone) through the terminal carboxyl group of the peptide chain or through a side chain carboxyl group present on an amino acid of the peptide. In a preferred embodiment, where the carboxyl pro-moiety group is a peptide, the carboxyl pro-moiety group is attached to β-lapachone through the terminal carboxyl group of the peptide chain.

Where the carboxyl pro-moiety group is an amino acid it may be selected from the group consisting of alanine, valine, leucine, isoleucine, phenylalanine, tryptophan, methionine, glycine, serine, threonine, cysteine, tyrosine, asparagine, glutamine, aspartic acid, glutamic acid, lysine, arginine, proline, and histidine. Where the carboxyl pro-moiety group is a carboxylic acid group it may be selected from the group consisting of —O(CO)—($C_1$-$C_{11}$)alkyl, —O(CO)—($C_0$-$C_6$)alkyl-(CO)—OH, —O(CO)—($C_0$-$C_6$)alkyl-aryl, —O(CO)—($C_0$-$C_6$)alkyl-aryl-heteroaryl, —O(CO)—($C_0$-$C_6$)alkyl-heteroaryl, and —O(CO)—($C_1$-$C_6$)alkyl-OH. Aryl and heteroaryl groups may be independently substituted with one or more independently selected $C_1$-$C_3$ alkyl groups.

In another embodiment, the carboxyl pro-moiety group may be a N-methyl amino acid, an N-ethyl amino acid, a N-methylated peptide, an N-ethylated peptide, or biotin.

In a preferred embodiment of the present invention, the pro-moiety is an amino acid moiety. Preferred prodrugs comprising an amino acid moiety are illustrated in Formula Ia below

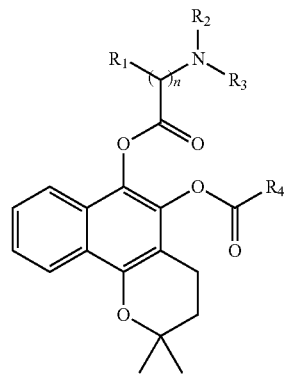

Formula Ia wherein
$R_1$ is independently selected from H; or alkyl, optionally substituted with a sulfyl (—SH or thio alkyl) group; or together with $R_2$ forms a saturated, unsaturated, or aromatic cyclic moiety;
$R_2$ and $R_3$ are independently H, alkyl, aromatic, or together form a saturated, unsaturated, or aromatic cyclic moiety;
$R_4$ is independently alkyl, aromatic, or can be a pro-moiety or form part of the amino acid moiety of the 1-carbonyl;
n is 1, 2, or 3.
In a further embodiment, $R_1$ is a ($C_1$-$C_4$) alcohol and $R_2$, $R_3$, $R_4$ and n are as described above.
The moiety

in Formula I and Formula Ia bears an $R_1$ group on each of the n=1 to n=3 carbons atom in parentheses. That moiety also bears a hydrogen atom (not shown) on each of the n=1 to n=3 carbons atom in parentheses as necessary to form properly tetravalent carbon atoms. A carbon atom in parentheses linked by a double bond to another atom need not bear any additional hydrogen atoms to be properly tetravalent. For example, when $R_1$ and $R_2$ taken together form a cyclic aromatic moiety, the carbon atom in parentheses need not bear an additional hydrogen atom.

In an alternative embodiment of compounds of Formula Ia, when an independently selected $R_1$ group is hydrogen or alkyl, the carbon atom to which it is immediately bound may bear an independently selected hydrogen or methyl group. For example, the partial structure of the

moiety from compounds of Formula Ia where n=2 can be represented as: —(C)$R_1$—(C)$R_1$—, and may be —C(H)($CH_3$)—C(H)($CH_3$)— when both independently selected $R_1$ groups are methyl, and may be —C($CH_3$)($CH_3$)—C($CH_2CH_3$)($CH_3$)— when $R_1$ is methyl in one instance and ethyl in the other instance, and each carbon bears an additional methyl group. In another example, when n=1, $R_1$ is methyl, and the carbon atom in parentheses bears an additional methyl group, then is —C(CH$_3$)$_2$—, as in examples 16 and 17, which exemplify the use of 2-methylalanine.

In another embodiment, the present invention includes compounds of Formula II:

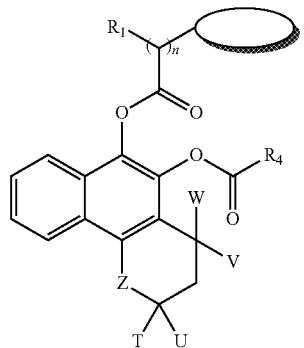

Formula II wherein

R$_1$ is independently selected from H; or alkyl, optionally substituted with a sulfyl (—SH or thio alkyl) group;

R$_4$ is independently alkyl, aromatic, or can be a pro-moiety, or form part of the pro-moiety of the 1-carbonyl;

n is 0, 1, 2, or 3, with the proviso that when n is 0, R$_1$ is not present;

Z is selected from the group consisting of carbon, nitrogen, oxygen, and sulfur; and T, U, V and W are independently selected from the group consisting of hydrogen and (C$_1$-C$_6$) alkyl.

In an embodiment, the present invention includes compounds of Formula II where Z is oxygen. Examplary compounds of Formula II where Z is oxygen are described above in Formulas I and Ia. In an embodiment of the present invention, compounds of Formula II are included where Z is sulfur.

In an embodiment, T is hydrogen. In another embodiment, U is hydrogen. In a further embodiment, both T and U are hydrogen. In an embodiment of the present invention, T is (C$_1$-C$_6$) alkyl. In another embodiment, U is (C$_1$-C$_6$) alkyl. In a further embodiment, both T and U are (C$_1$-C$_6$) alkyl. In another embodiment of the present invention, T is methyl. In another embodiment, U is methyl. In a further embodiment, both T and U are methyl.

In an embodiment of the present invention, V is hydrogen. In another embodiment, W is hydrogen. In a further embodiment, V and W are hydrogen. In an embodiment of the present invention, V is (C$_1$-C$_6$) alkyl. In another embodiment, W is (C$_1$-C$_6$) alkyl. In a further embodiment, both V and W are (C$_1$-C$_6$) alkyl. In another embodiment of the present invention, V is methyl. In another embodiment, W is methyl. In a further embodiment, both V and W are methyl.

In an embodiment, Z is sulfur, T and U are hydrogen, and V and W are independently selected (C$_1$-C$_6$) alkyl groups.

In an embodiment of the present invention, the pro-moiety is an amino acid moiety. Exemplary prodrugs comprising an amino acid moiety are illustrated in Formula IIa below

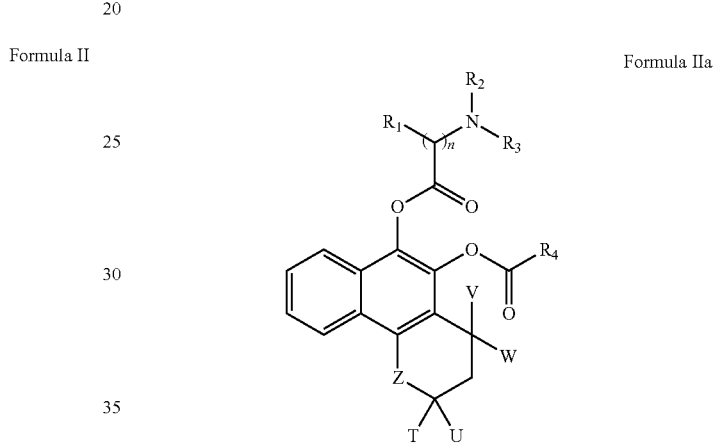

Formula IIa wherein

R$_1$ is independently selected from H; or alkyl, optionally substituted with a sulfyl (—SH or thio alkyl) group; or together with R$_2$ forms a saturated, unsaturated, or aromatic cyclic moiety;

R$_2$ and R$_3$ are independently H, alkyl, aromatic, or together form a saturated, unsaturated, or aromatic cyclic moiety;

R$_4$ is independently alkyl, aromatic, or can be a pro-moiety or form part of the amino acid moiety of the 1-carbonyl;

n is 1, 2, or 3;

Z is selected from the group consisting of carbon, nitrogen, oxygen, and sulfur; and T, U, V and W are independently selected from the group consisting of hydrogen and (C$_1$-C$_6$) alkyl.

In an embodiment, compounds of Formula Ia are included where R$_2$ and R$_3$ are hydrogen. In a further embodiment of the present invention, compounds of Formula Ia are included where R$_1$, R$_2$, and R$_3$ are hydrogen.

Certain preferred β-lapachone prodrug compositions include Prodrug 1 through Prodrug 28, as illustrated in the table below.

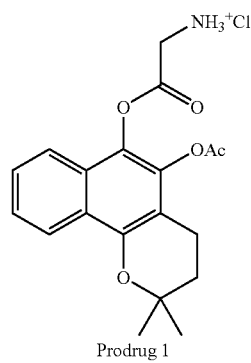
Prodrug 1
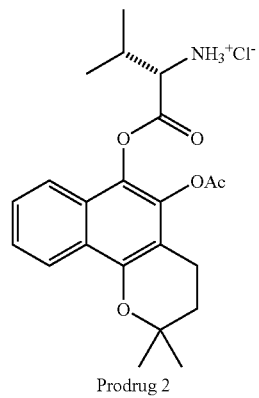
Prodrug 2
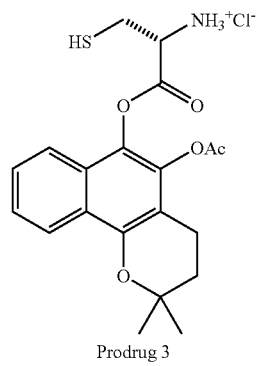
Prodrug 3
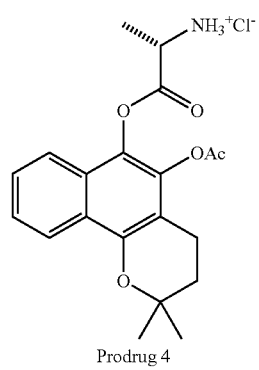
Prodrug 4

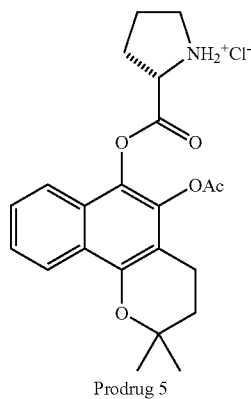
Prodrug 5
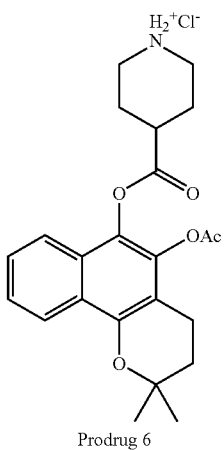
Prodrug 6
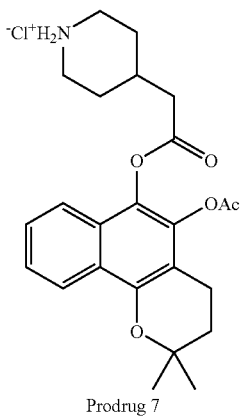
Prodrug 7
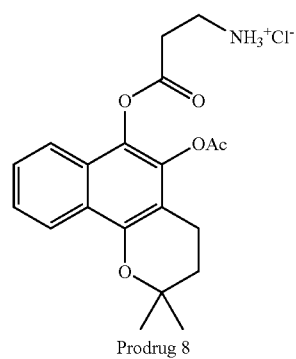
Prodrug 8

-continued
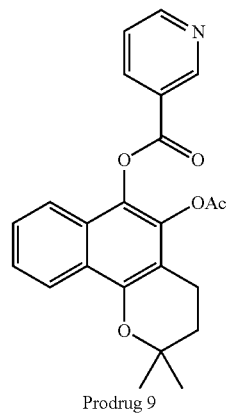 [SMILES: CC(=O)Oc1c2c(c3ccccc3c1OC(=O)c1cccnc1)OC(C)(C)CC2]
Prodrug 9
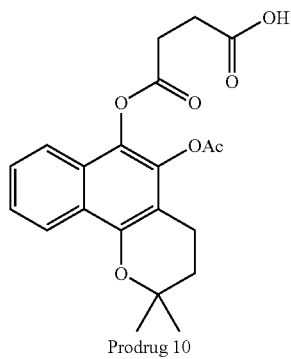 [SMILES: CC(=O)Oc1c2c(c3ccccc3c1OC(=O)CCC(=O)O)OC(C)(C)CC2]
Prodrug 10
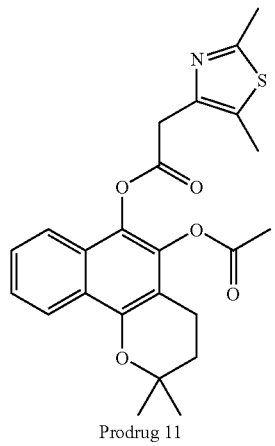 [SMILES: CC(=O)Oc1c2c(c3ccccc3c1OC(=O)Cc1nc(C)sc1C)OC(C)(C)CC2]
Prodrug 11
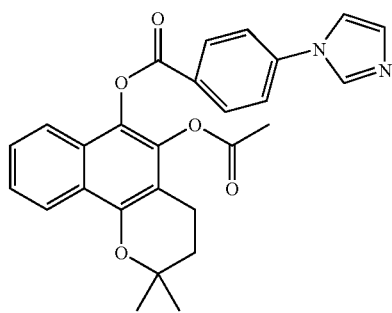
Prodrug 12

-continued
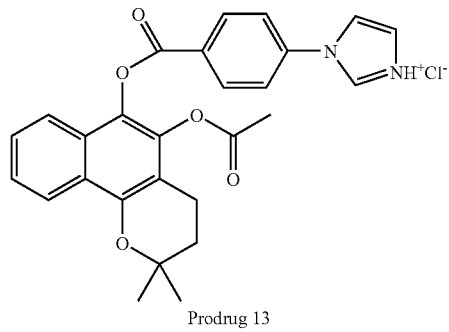
Prodrug 13
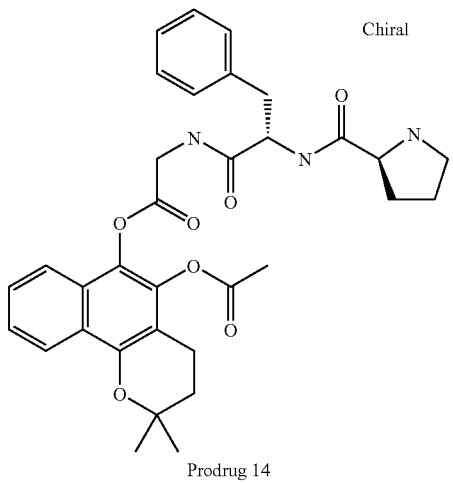 [SMILES: CC(=O)Oc1c2c(c3ccccc3c1OC(=O)CNC(=O)[C@H](Cc1ccccc1)NC(=O)[C@@H]1CCCN1)OC(C)(C)CC2]
Prodrug 14
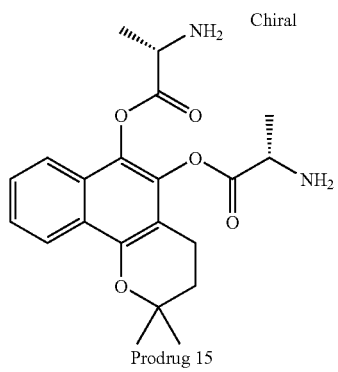 [SMILES: C[C@H](N)C(=O)Oc1c2c(c3ccccc3c1OC(=O)[C@H](C)N)OC(C)(C)CC2]
Prodrug 15
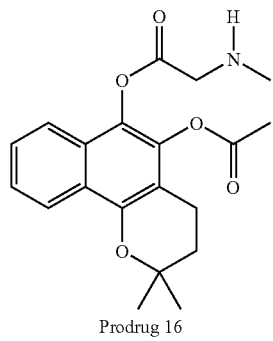 [SMILES: CNCC(=O)Oc1c(OC(C)=O)c2c(c3ccccc13)OC(C)(C)CC2]
Prodrug 16

-continued
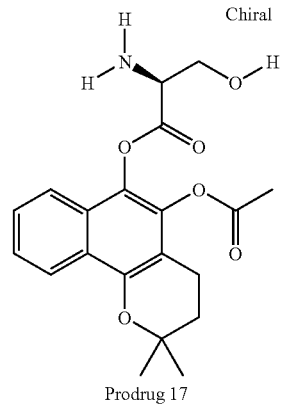 [SMILES: CC(=O)Oc1c2c(c3ccccc3c1OC(=O)[C@@H](N)CO)OC(C)(C)CC2]
Prodrug 17
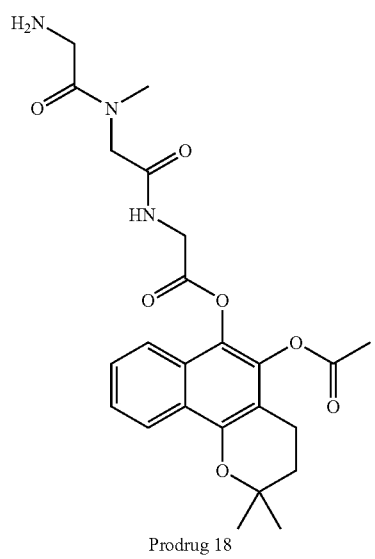 [SMILES: CC(=O)Oc1c2c(c3ccccc3c1OC(=O)CNC(=O)CN(C)C(=O)CN)OC(C)(C)CC2]
Prodrug 18
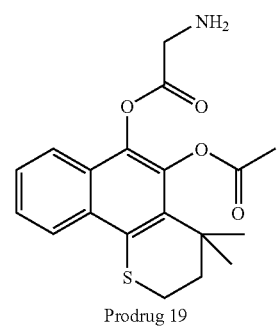 [SMILES: CC(=O)Oc1c2c(c3ccccc3c1OC(=O)CN)SCCC2(C)C]
Prodrug 19

-continued
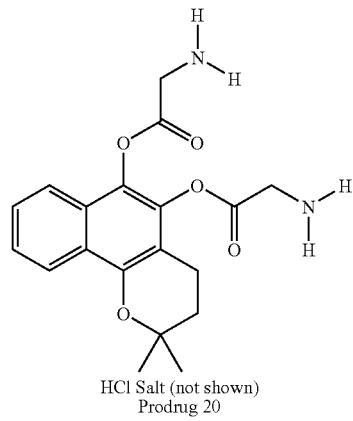 [SMILES: CC1(C)CCc2c(OC(=O)CN)c(OC(=O)CN)c3ccccc3c2O1]
HCl Salt (not shown)
Prodrug 20
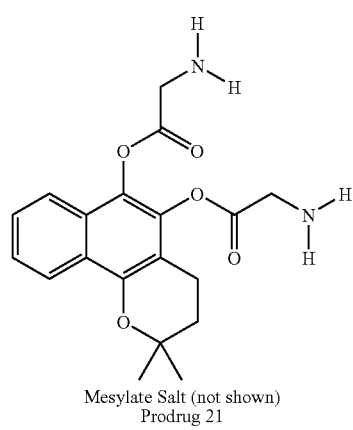 [SMILES: CC1(C)CCc2c(OC(=O)CN)c(OC(=O)CN)c3ccccc3c2O1]
Mesylate Salt (not shown)
Prodrug 21
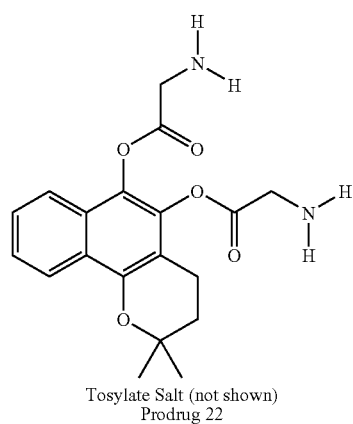 [SMILES: CC1(C)CCc2c(OC(=O)CN)c(OC(=O)CN)c3ccccc3c2O1]
Tosylate Salt (not shown)
Prodrug 22

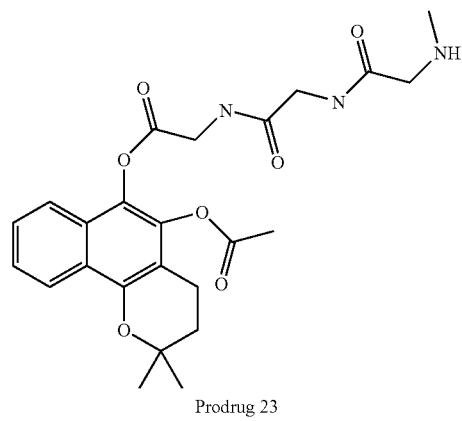 [SMILES: CNCC(=O)NCC(=O)NCC(=O)Oc1c(OC(C)=O)c2c(c3ccccc13)OC(C)(C)CC2]
Prodrug 23
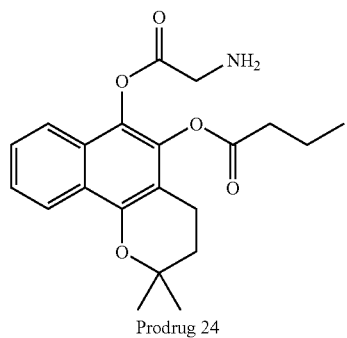 [SMILES: CCCC(=O)Oc1c2c(c3ccccc3c1OC(=O)CN)OC(C)(C)CC2]
Prodrug 24
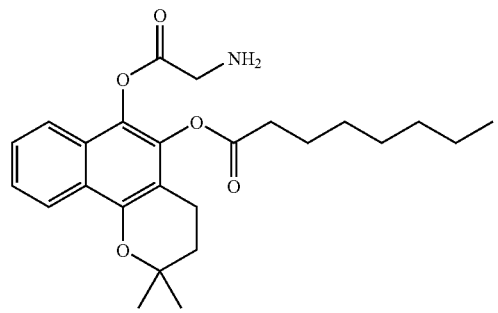
Prodrug 25
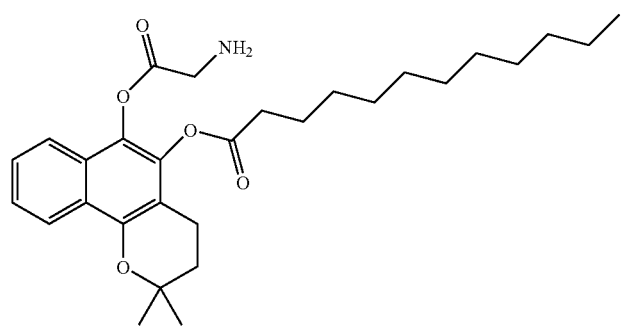
Prodrug 26

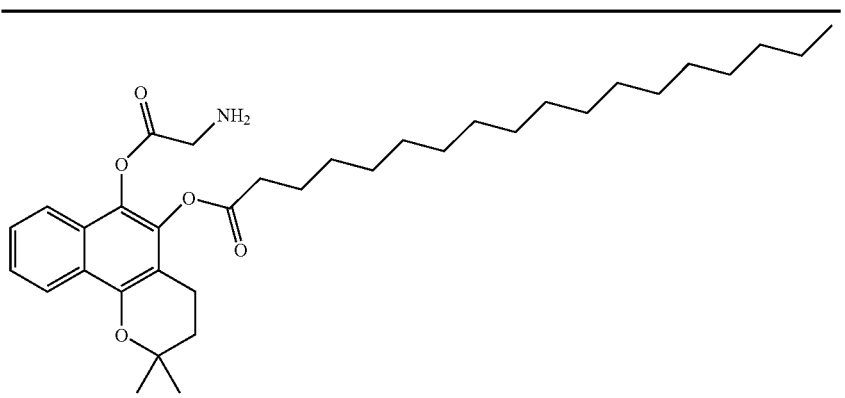

Prodrug 27

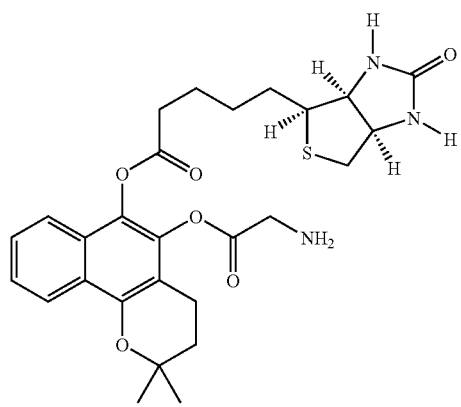

Prodrug 28

Other preferred prodrug compositions include those described in the examples.

The quinone prodrug compositions of the invention may be prepared in any manner known in the art. For example, the β-lapachone prodrug compositions of Formula Ia may be prepared in accordance with Scheme Ia, illustrated below. However, many modifications can be made to the synthesis scheme, as recognized by those skilled in the art.

Scheme Ia

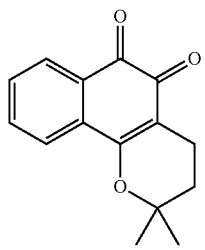

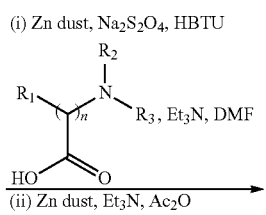

Compound 1

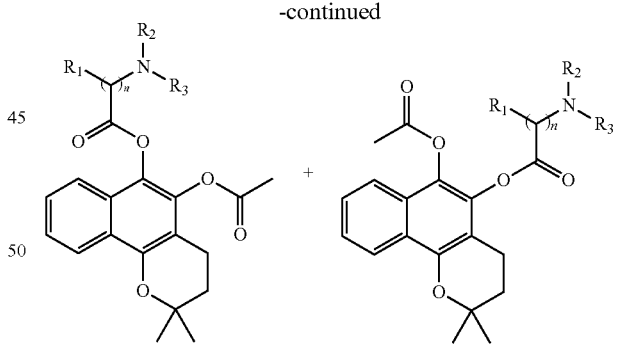

Major Product
Prodrug A

Minor Product
Prodrug B

If substitution of the amino acid moiety at both quinone carbonyl groups is desired, two eqivalents of the amino acid moiety may be used under conditions similar to those depicted in Scheme Ia. Further, protecting groups may be used if desired under the reaction conditions.

D. Methods of the Invention

In another aspect, the present invention relates to therapeutic methods. The methods of the invention can by used to treat or prevent any disease or condition in which the quinone compound is useful. In particular, the methods of the invention relate to the treatment of cancer.

More particularly, one embodiment of the invention relates to methods for treating cancer comprising administering a composition comprising a therapeutically effective amount of at least one quinone prodrug composition of the invention to a subject in need thereof. In a particularly preferred embodiment, the quinone prodrug composition comprises a napthoquinone, such as a 1,2-napthoquinone including β-lapachone and analogs thereof.

Another aspect of the invention relates to methods for obtaining improved plasma half-life of quinone compounds in vivo comprising administering a therapeutically effective amount of at least one quinone prodrug composition of the invention to a subject in need thereof, wherein the quinone prodrug exhibits an improved plasma half-life in vivo as compared to administration of the quinone compound not in a prodrug form. Again, in a particularly preferred embodiment, the quinone prodrug composition comprises a napthoquinone, such as a 1,2-napthoquinone including β-lapachone and analogs thereof.

In preferred embodiments, the methods of the invention are particularly useful for the treatment of mammalian cancers, including lung, breast, colon, ovarian and prostate cancers, multiple myeloma and malignant melanoma, or for improving the accumulation of drug in such cancer tissues.

According to the methods of the invention, the compound(s) may be administered to the subject via any drug delivery route known in the art. Specific exemplary administration routes include peripheral and central routes such as oral, ocular, rectal, buccal, topical, nasal, ophthalmic, subcutaneous, intramuscular, intraveneous (bolus and infusion), intracerebral, transdermal, and pulmonary. The quinone prodrug compositions of the invention are particularly suited for oral or parenteral administration.

The term "therapeutically effective amount", as used herein, refers to an amount of a pharmaceutical agent to treat, ameliorate, or prevent the identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The dosage may vary within this range depending upon the dosage form employed, sensitivity of the patient, and the route of administration.

The compounds of the invention may be administered at doses that vary from 0.1 μg to 100,000 mg, depending upon the route of administration. The preferred dose will be in the range of about 0.1 mg/day to about 10 g/day, or more preferably about 0.1 mg to about 3 g/day, or still more about 0.1 mg to about 1 g/day, in single, divided, or continuous doses (which dose may be adjusted for the patient's weight in kg, body surface area in $m^2$, and age in years).

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

E. Metabolites of the Compounds of the Invention

Also falling within the scope of the present invention are the in vivo metabolic products of the quinone prodrug compositions of the invention, particularly β-lapachone prodrug compositions described herein. Metabolites of the prodrug compounds of the invention include the active moiety released from the prodrug following administration to a subject, including the base quinone such as the β-lapachone compounds described herein. Such products may result for example from the oxidation, reduction, hydrolysis, amidation, esterification and the like of the administered compound, primarily due to enzymatic processes. Accordingly, the invention includes compounds produced by a process comprising contacting a quinone prodrug composition of the invention with a mammalian tissue or a mammal for a period of time sufficient to yield a metabolic product thereof.

Such products typically are identified by preparing a radio-labeled (e.g. $^{14}C$ and/or $^{3}H$) prodrug of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood, tumor, or other biological samples. These products are easily isolated since they are radio-labeled. The metabolite structures are determined in conventional fashion, e.g., by MS, MS/MS, or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

F. Pharmaceutical Compositions of the Invention

In yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3.0 to a pH of about 11.0, depending on the formulation, route of administration, and any other factors required to deliver a therapeutically effective dosage.

More particularly, the pharmaceutical compositions of the invention comprise a therapeutically effective amount of at least one quinone prodrug composition of the present invention, together with one or more pharmaceutically acceptable excipients. When the pharmaceutical composition is formulated, the composition preferably comprises from about 0.1 mg/ml to about 50 mg/ml of the quinone prodrug composition.

Optionally, the pharmaceutical compositions of the invention may comprise a combination of quinone prodrug compositions of the present invention, or may include a second therapeutic agent useful in the treatment of cancer. Therapeutic amounts of second agents are generally known in the art or may be determined by the skilled clinician.

Formulations of the present invention, e.g., for parenteral or oral administration, are most typically solids, liquid solutions, emulsions or suspensions, while inhaleable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exist a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

G. Combination Therapy

It is also possible to combine any quinone prodrug composition of the present invention with one or more other active agents useful in the treatment of the target disease or disorder such as cancer, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the activity of the quinone prodrug composition of the invention. Examples of second anticancer agents include, but are not limited to, taxane derivatives such as paclitaxel and docetaxol; gemcitabine (Gemzar®), other nucleoside and nucleotide anticancer agents; cisplatin (Platinol®); targeted agents such as imatnibmeasylate (Gleevec®) and trastuzumab (Herceptin®); or any other anticancer agent approved for therapeutic use in humans. Further anticancer agents useful in combination therapies are disclosed, e.g., in U.S. 2004/0087610 A1, which is herein incorporated by reference.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

A. Example 1

Synthesis of 5-(acetyloxy)-2,2-dimethyl-3,4-dihydro-2H-benzo[h]chromen-6-yl N-(tert-butoxycarbonyl)glycinate (1)

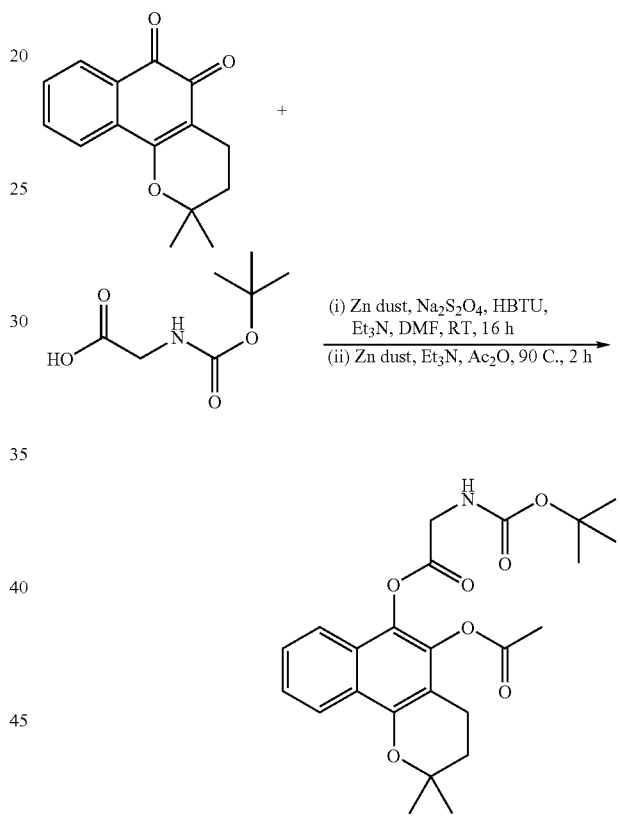

5-(acetyloxy)-2,2-dimethyl-3,4-dihydro-2H-benzo[h] chromen-6-yl N-(tert-butoxycarbonyl)glycinate (1). A mixture of zinc dust (6.0 g, 91.7 mmol), 2,2-dimethyl-3,4-dihydro-2H-benzo[h]chromene-5,6-dione (6.0 g, 24.8 mmol), $Na_2S_2O_4$ (17.26 g, 99.1 mmol), N-(tert-butoxycarbonyl)glycine (8.77 g, 49.6 mmol), triethylamine (3.1 mL, 22.3 mmol), HBTU (18.79 g, 49.6 mmol) and DMF (100 mL) is stirred for 16 hours at room temperature. To the reaction mixture is then added EtOAc (300 mL). The reaction is filtered and the filtrate washed with $H_2O$ (4×200 mL). The organic extract is dried with $Na_2SO_4$ and concentrated under reduced pressure. The residue is dissolved in acetic anhydride (30 mL) followed by the addition of zinc dust (3.0 g, 45.9 mmol) and thriethylamine (3.35 mL, 24.0 mmol). The reaction is heated at 90° C. with vigorous stirring and held for 2 hours. The reaction is allowed to cool and the solvent removed under reduced pressure. The residue is dissolved in EtOAc (200 mL) and washed with water (2×100 mL). The organic extract is dried with $Na_2SO_4$ and concentrated under reduced pressure. The crude product is purified by flash column chromatography ($SiO_2$, 2% EtOAc in dichloromethane) to afford about 60% pure final product. Crystallization of the partly pure solid from EtOAc/Hexane gives the desired product as pure white solid (3.2 g, 31%). M.p.=177° C.; 400 MHz $^1$H NMR (CDCl$_3$) δ: 8.21 (d, J=8.4 Hz, 1H), 7.67 (d, J=8.4 Hz, 1H), 7.46 (m, 2H), 5.13 (br. s, 1H), 4.30 (d, J=5.6 Hz, 2H), 2.68 (t, J=6.6 Hz, 2H), 2.38 (s, 3H), 1.87 (t, J=6.6 Hz, 2H), 1.48 (s, 9H), 1.42 (s, 6H); LCMS: 444 [M+H]; Calc. for $C_{24}H_{29}NO_7$: C, 64.94; H, 6.59; N, 3.16; Found C 64.98, H 6.51, N 3.15.

B. Example 2

Synthesis of 5-(acetyloxy)-2,2-dimethyl-3,4-dihydro-2H-benzo[h]chromen-6-yl glycinate hydrochloride (2)

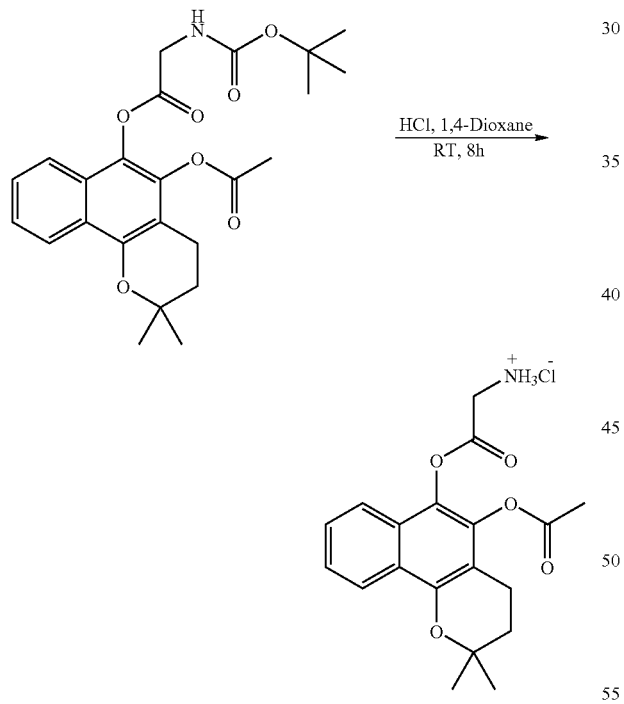

Synthesis of 5-(acetyloxy)-2,2-dimethyl-3,4-dihydro-2H-benzo[h]chromen-6-yl glycinate hydrochloride (2—Prodrug 1): To a solution of 5-(acetyloxy)-2,2-dimethyl-3,4-dihydro-2H-benzo[h]chromen-6-yl N-(tert-butoxycarbonyl)glycinate (1) (2.35 g, 4.0 mmol) in 1,4-dioxane (25 mL) is added a solution of hydrogen chloride gas in anhydrous 1,4-dioxane (4.0 M, 60 mL). The reaction is stirred at room temperature for 6 hours. The reaction is dried under reduced pressure. The product is obtained as a white solid (1.489 g, 95%) M.p.=176-178° C.; 400 MHz $^1$H NMR (DMSO-d$_6$) δ: 8.58 (br. s, 3H), 8.14 (m, 1H), 7.9 (m, 1H), 7.55 (m, 2H), 4.41 (s, 2H), 2.62 (t, J=6.6 Hz, 2H), 2.41 (s, 3H), 1.88 (t, J=6.6 Hz, 2H), 1.39 (s, 6H); LCMS: 344 [M+H]; Calc. for $C_{19}H_{21}NO_5 \cdot 1.25$ HCl: C, 58.62; H, 5.77; N, 3.6; Found C, 58.7; H, 5.72; N, 3.47.

C. Example 3

Synthesis of 5-(acetyloxy)-2,2-dimethyl-3,4-dihydro-2H-benzo[h]chromen-6-yl N-(tert-butoxycarbonyl)-L-alaninate (3) and 6-(acetyloxy)-2,2-dimethyl-3,4-dihydro-2H-benzo[h]chromen-5-yl N-(tert-butoxycarbonyl)-L-alaninate (4)

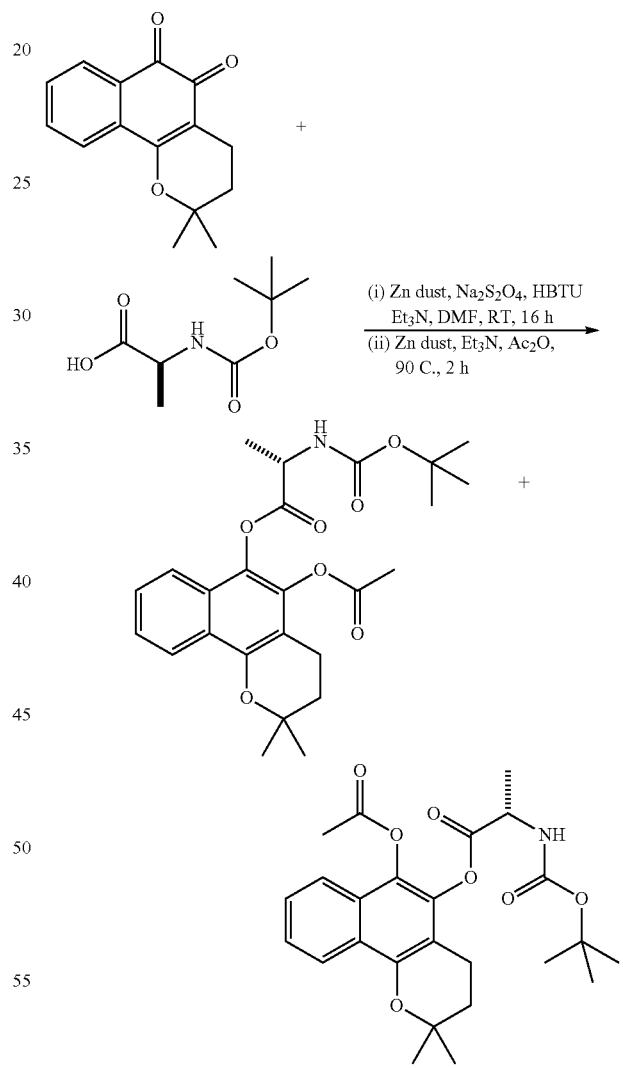

5-(acetyloxy)-2,2-dimethyl-3,4-dihydro-2H-benzo[h]chromen-6-yl N-(tert-butoxycarbonyl)-L-alaninate (3) and 6-(acetyloxy)-2,2-dimethyl-3,4-dihydro-2H-benzo[h]chromen-5-yl N-(tert-butoxycarbonyl)-L-alaninate (4). The compounds 5-(acetyloxy)-2,2-dimethyl-3,4-dihydro-2H-benzo[h]chromen-6-yl N-(tert-butoxycarbonyl)-L-alaninate (3) and 6-(acetyloxy)-2,2-dimethyl-3,4-dihydro-2H-benzo

[h]chromen-5-yl N-(tert-butoxycarbonyl)-L-alaninate (4) are synthesized as described in example 1 using zinc dust (2.0 g, 30.5 mmol), 2,2-dimethyl-3,4-dihydro-2H-benzo[h]chromene-5,6-dione (2.0 g, 8.26 mmol), $Na_2S_2O_4$ (5.75 g, 33.0 mmol), N-(tert-butoxycarbonyl)-L-alanine (3.12 g, 16.51 mmol), triethylamine (1.04 mL, 7.43 mmol), HBTU (6.26 g, 16.5 mmol) and DMF (20 mL) for the 1$^{st}$ step. The acetylation step is carried out using zinc dust (1.0 g, 15.3 mmol), thriethylamine (1.04 mL, 7.43 mmol) and acetic anhydride (30 mL). Both the compounds are generated in the reaction. The crude mixture is purified by three consecutive flash column chromatography on $SiO_2$ (twice using a gradient from 10% EtOAc in hexanes to 25% EtOAc in hexanes once using 100% dichloromethane) to afford pure desired product (1.37 g, 36%) as mixture of isomers (3:4) in a ratio of 2.8:1, as established by $^1$H NMR. M.p.=94-98° C.; 400 MHz $^1$H NMR ($CDCl_3$), major isomer δ:8.21 (d, J=8.8 Hz, 1H), 7.69 (d, J=8.8 Hz, 1H), 7.45 (m, 2H), 5.10 (d, J=8.4 Hz, 1H), 4.71 (dd, J=7.6, 7.6 Hz, 1H), 2.68 (t, J=6.8 Hz, 2H), 2.37 (s, 3H), 1.87 (t, J=6.8 Hz, 2H), 1.67 (d, J=7.2 Hz, 3H), 1.48 (s, 9H), 1.42 (s, 6H); minor isomer δ: 8.20 (d, J=7.6 Hz, 1H), 7.67 (d, J=7.6 Hz, 1H), 7.45 (m, 2H), 5.09 (d, J=9.2 Hz, 1H), 4.64 (dd, J=8.4, 7.6 Hz, 1H), 2.67 (t, J=6.8 Hz, 2H), 2.43 (s, 3H), 1.87 (t, J=6.8 Hz, 2H), 1.61 (d, J=6.8 Hz, 3H), 1.48 (s, 9H), 1.42 (s, 6H); LCMS: 458 [M+H]; Calc. for $C_{25}H_{31}NO_7 \cdot 0.7H_2O \cdot 0.4 CH_2Cl_2$: C, 60.46; H, 6.64; N, 2.79; Found C, 60.46; H, 6.60; N, 3.02.

D. Example 4

Synthesis of 5-(acetyloxy)-2,2-dimethyl-3,4-dihydro-2H-benzo[h]chromen-6-yl L-alaninate hydrochloride (5) and 6-(acetyloxy)-2,2-dimethyl-3,4-dihydro-2H-benzo[h]chromen-5-yl L-alaninate hydrochloride (6)

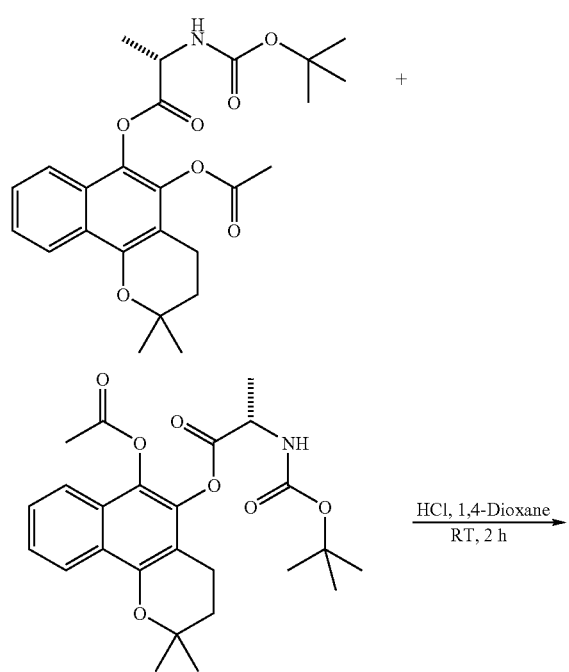

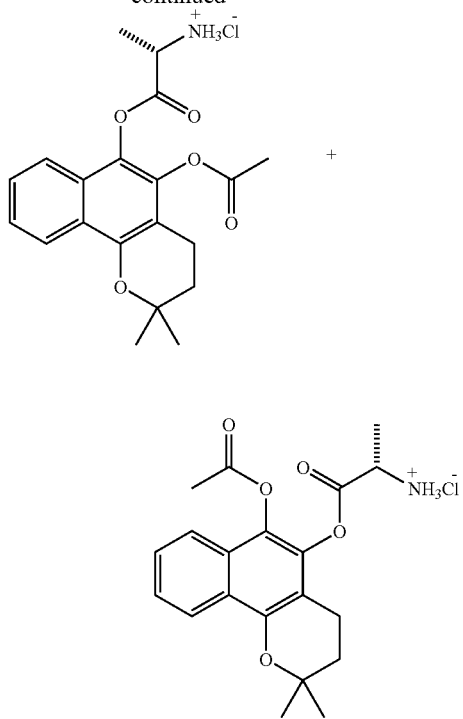

5-(acetyloxy)-2,2-dimethyl-3,4-dihydro-2H-benzo[h]chromen-6-yl L-alaninate hydrochloride (5—Prodrug 4) and 6-(acetyloxy)-2,2-dimethyl-3,4-dihydro-2H-benzo[h]chromen-5-yl L-alaninate hydrochloride (6). To a solution of 5-(acetyloxy)-2,2-dimethyl-3,4-dihydro-2H-benzo[h]chromen-6-yl N-(tert-butoxycarbonyl)-L-alaninate (3) and 6-(acetyloxy)-2,2-dimethyl-3,4-dihydro-2H-benzo[h]chromen-5-yl N-(tert-butoxycarbonyl)-L-alaninate (4) (1.3 g, 2.84 mmol) in 1,4-dioxane (5 mL) is added a solution of hydrogen chloride gas in anhydrous 1,4-dioxane (4.0 M, 20 mL). The reaction is stirred at room temperature for 30 minutes. The reaction is dried under reduced pressure resulting in a pale yellow solid. The solid is triturated with $Et_2O$ to afford the desired product as an off white solid (1.11 g, 99%) and is a mixture of both the isomers 5-(acetyloxy)-2,2-dimethyl-3,4-dihydro-2H-benzo[h]chromen-6-yl L-alaninate hydrochloride (5) and 6-(acetyloxy)-2,2-dimethyl-3,4-dihydro-2H-benzo[h]chromen-5-yl L-alaninate hydrochloride (6). The ratio of the isomers 5:6 is determined to be 4:1 by $^1$H NMR. M.p.=229-230° C.; 400 MHz $^1$H NMR (DMSO-d$_6$), major isomer δ: 8.80 (br. s, 3H), 8.15 (d, J=8.4 Hz, 1H), 7.88 (d, J=8.4 Hz, 1H), 7.57 (m, 2H), 4.69 (q, J=7.2 Hz, 1H), 2.64 (m, 2H), 2.39 (s, 3H), 1.88 (t, J=6.6 Hz, 2H), 1.69 (d, J=7.2 Hz, 3H), 1.40 (s, 6H); minor isomer δ: 8.80 (br. s, 3H), 8.14 (d, J=8.1 Hz, 1H), 7.79 (d, J=8.0 Hz, 1H), 7.57 (m, 2H), 4.60 (q, J=7.2 Hz, 1H), 2.64 (m, 2H), 2.45 (s, 3H), 1.88 (t, J=6.6 Hz, 2H), 1.66 (d, J=7.2 Hz, 3H), 1.39 (s, 6H); LCMS: 358 [M+H];

Calc. for C$_{20}$H$_{23}$NO$_5$.1.11 HCl: C, 60.32; H, 6.11; N, 3.52; Found C 60.40, H 6.17, N 3.43.

E. Example 5

Synthesis of 5-(acetyloxy)-2,2-dimethyl-3,4-dihydro-2H-benzo[h]chromen-6-yl N-(tert-butoxycarbonyl)-L-valinate (7) and 6-(acetyloxy)-2,2-dimethyl-3,4-dihydro-2H-benzo[h]chromen-5-yl N-(tert-butoxycarbonyl)-L-valinate (8)

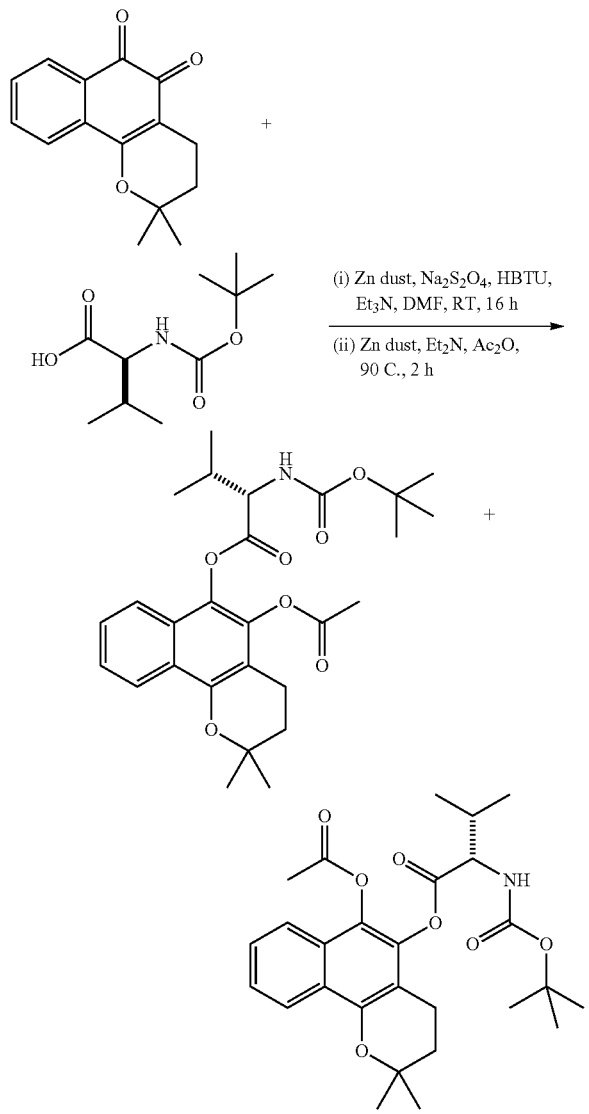

5-(acetyloxy)-2,2-dimethyl-3,4-dihydro-2H-benzo[h]chromen-6-yl N-(tert-butoxycarbonyl)-L-valinate (7) and 6-(acetyloxy)-2,2-dimethyl-3,4-dihydro-2H-benzo[h]chromen-5-yl N-(tert-butoxycarbonyl)-L-valinate (8). The compounds 5-(acetyloxy)-2,2-dimethyl-3,4-dihydro-2H-benzo[h]chromen-6-yl N-(tert-butoxycarbonyl)-L-valinate (7) and 6-(acetyloxy)-2,2-dimethyl-3,4-dihydro-2H-benzo[h]chromen-5-yl N-(tert-butoxycarbonyl)-L-valinate (8) are synthesized as described in example 1 using zinc dust (3.0 g, 46 mmol), 2,2-dimethyl-3,4-dihydro-2H-benzo[h]chromene-5,6-dione (3.0 g, 12.4 mmol), Na$_2$S$_2$O$_4$ (g, mmol), N-(tert-butoxycarbonyl)-L-valine (8.6 g, 49.5 mmol), triethylamine (1.5 mL, 10.7 mmol), HBTU (9.3 g, 24.6 mmol) and DMF (30 mL) for the 1$^{st}$ step. The acetylation step is carried out using zinc dust (1.5 g, 23 mmol), thriethylamine (3.3 mL, 23.7 mmol) and acetic anhydride (30 mL). Both the compounds are generated in the reaction. The crude mixture is purified by flash column chromatography (SiO$_2$, 1% EtOAc in dichloromethane to 5% EtOAc in dichloromethane) to afford pure desired products (1.02 g, 17%) as mixture of isomers (7:8) in a ratio of 2.8:1 as established by $^1$H NMR. Mixture of two isomers, ratio by NMR=2.8:1. M.p.=74-76° C.; 400 MHz $^1$H NMR (CDCl$_3$), major isomer δ: 8.21 (d, J=8.1 Hz, 1H), 7.70 (d, J=7.7 Hz, 1H), 7.45 (m, 2H), 5.08 (d, J=9.9 Hz, 1H), 4.65 (dd, J=9.5, 4.4 Hz, 1H), 2.67 (t, J=6.8 Hz, 2H), 2.54-2.40 (m, 1H), 2.35 (s, 3H), 1.87 (t, J=6.8 Hz, 2H), 1.48 (s, 9H), 1.43 (s, 6H), 1.17 (d, J=7.0 Hz, 3H), 1.09 (d, J=7.0 Hz, 3H); minor isomer δ: 8.21 (d, J=8.1 Hz, 1H), 7.65 (d, J=7.3 Hz, 1H), 7.45 (m, 2H), 5.07 (d, J=11.7 Hz, 1H), 4.56 (dd, J=9.9, 4.4 Hz, 1H), 2.67 (t, J=6.8 Hz, 2H), 2.54-2.40 (m, 1H), 2.42 (s, 3H), 1.87 (t, J=6.8 Hz, 2H), 1.48 (s, 9H), 1.41 (s, 6H), 1.14 (d, J=7.0 Hz, 3H), 1.06 (d, J=7.0 Hz, 3H).

F. Example 6

Synthesis of 5-(acetyloxy)-2,2-dimethyl-3,4-dihydro-2H-benzo[h]chromen-6-yl L-valinate hydrochloride (9) and 6-(acetyloxy)-2,2-dimethyl-3,4-dihydro-2H-benzo[h]chromen-5-yl L-valinate hydrochloride (10)

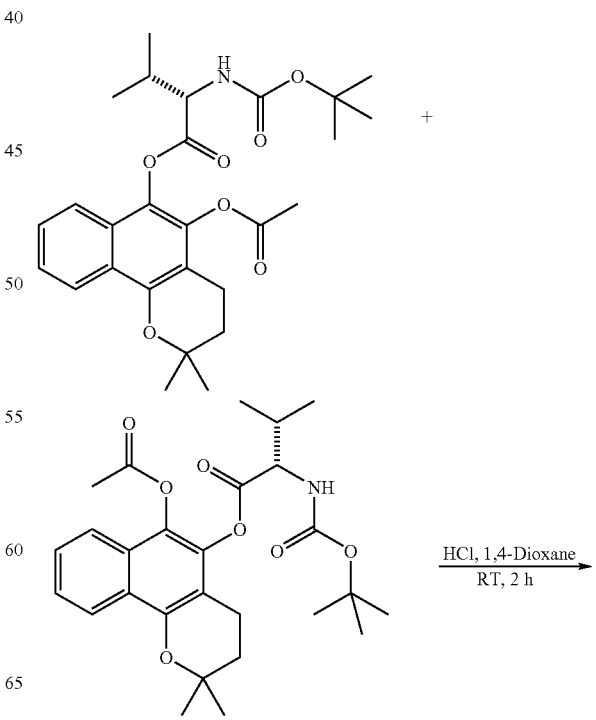

-continued

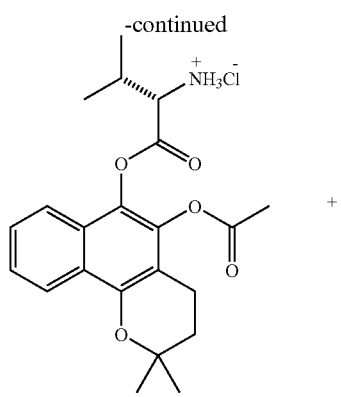

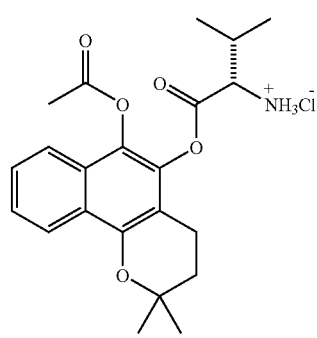

5-(acetyloxy)-2,2-dimethyl-3,4-dihydro-2H-benzo[h]chromen-6-yl L-valinate hydrochloride (9—Prodrug 2) and 6-(acetyloxy)-2,2-dimethyl-3,4-dihydro-2H-benzo[h]chromen-5-yl L-valinate hydrochloride (10). To a solution of 5-(acetyloxy)-2,2-dimethyl-3,4-dihydro-2H-benzo[h]chromen-6-yl N-(tert-butoxycarbonyl)-L-valinate (7) and 6-(acetyloxy)-2,2-dimethyl-3,4-dihydro-2H-benzo[h]chromen-5-yl N-(tert-butoxycarbonyl)-L-valinate (8) (0.95 g, 1.95 mmol) in 1,4-dioxane (5 mL) is added a solution of hydrogen chloride gas in anhydrous 1,4-dioxane (4.0 M, 10 mL). The reaction is stirred at room temperature for 4 hours. The reaction is dried under reduced pressure. The product is obtained as a white solid (0.72 g, 95%) and is a mixture of both the isomers 5-(acetyloxy)-2,2-dimethyl-3,4-dihydro-2H-benzo[h]chromen-6-yl L-valinate hydrochloride (9) and 6-(acetyloxy)-2,2-dimethyl-3,4-dihydro-2H-benzo[h]chromen-5-yl L-valinate hydrochloride (10). The ratio of the isomers 9:10 is determined to be 4:1 by $^1$H NMR. Mixture of two isomers, ratio by NMR=4:1. M.p.=149-151° C.; 400 MHz $^1$H NMR (DMSO-$d_6$), major isomer δ: 8.79 (br. s, 3H), 8.15 (d, J=6.8 Hz, 1H), 7.91 (d, J=7.6 Hz, 1H), 7.60 (m, 2H), 4.59 (d, J=3.2 Hz, 1H), 3.4-3.2 (m, 2H), 2.7-2.5 (m, 1H), 2.38 (s, 3H), 1.89 (m, 2H), 1.39 (s, 6H), 1.14 (m, 6H); minor isomer δ: 8.79 (br. s, 3H), 8.15 (d, J=6.8 Hz, 1H), 7.78 (d, J=7.8 Hz, 1H), 7.60 (m, 2H), 4.48 (d, J=3.6 Hz, 1H), 3.4-3.2 (m, 2H), 2.7-2.5 (m, 1H), 2.45 (s, 3H), 1.89 (m, 2H), 1.41 (s, 6H), 1.14 (m, 6H); LCMS: 386 [M+H]; Calc. for $C_{22}H_{27}NO_5 \cdot 1.25$ HCl: C, 61.25; H, 6.60; N, 3.24; Found C 61.06, H 6.41, N 3.22.

G. Example 7

Synthesis of 2-[5-(acetyloxy)-2,2-dimethyl-3,4-dihydro-2H-benzo[h]chromen-6-yl] 1-tert-butyl (2S)-pyrrolidine-1,2-dicarboxylate (11) and 2-[6-(acetyloxy)-2,2-dimethyl-3,4-dihydro-2H-benzo[h]chromen-5-yl]1 1-tert-butyl (2S)-pyrrolidine-1,2-dicarboxylate (12)

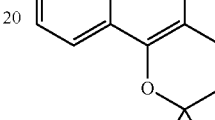

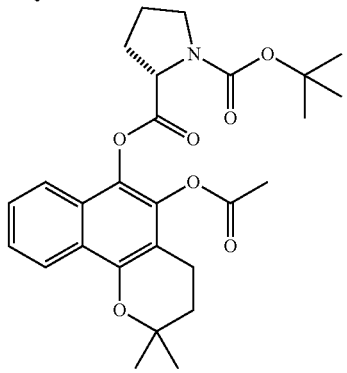

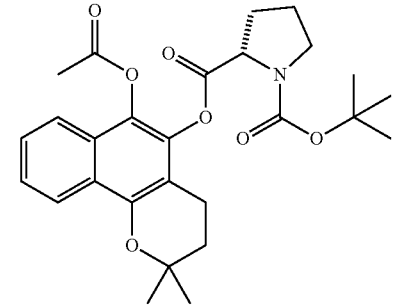

2-[5-(acetyloxy)-2,2-dimethyl-3,4-dihydro-2H-benzo[h]chromen-6-yl] 1-tert-butyl (2S)-pyrrolidine-1,2-dicarboxylate (11) and 2-[6-(acetyloxy)-2,2-dimethyl-3,4-dihydro-2H-benzo[h]chromen-5-yl] 1-tert-butyl (2S)-pyrrolidine-1,2-dicarboxylate (12). The compounds 2-[5-(acetyloxy)-2,2-dimethyl-3,4-dihydro-2H-benzo[h]chromen-6-yl] 1-tert-butyl (2S)-pyrrolidine-1,2-dicarboxylate (11) and 2-[6-(acetyloxy)-2,2-dimethyl-3,4-dihydro-2H-benzo[h]chromen-5-yl] 1-tert-butyl (2S)-pyrrolidine-1,2-dicarboxylate (12) are synthesized as described in example 1 using zinc dust (3.0 g, 45.9 mmol), 2,2-dimethyl-3,4-dihydro-2H-benzo[h]chromene-5,6-dione (3.0 g, 12.39 mmol), Na$_2$S$_2$O$_4$ (8.77 g, 49.6 mmol), N-(tert-butoxycarbonyl)-L-proline (8.0 g, 37.2 mmol), triethylamine (2.6 mL, 18.6 mmol), HBTU (14.1 g, 37.2 mmol) and DMF (80 mL) for the 1$^{st}$ step. The acetylation step is carried out using zinc dust (1.5 g, 18.6 mmol), thriethylamine (2.6 mL, 18.6 mmol) and acetic anhydride (40 mL). Both the compounds are generated in the reaction. The two isomers in the crude mixture are separated by two consecutive flash column chromatography on SiO$_2$ (1$^{st}$ purification is carried out using a step gradient from 100% dichloromethane to 2% EtOAc in dichloromethane and 2$^{nd}$ purification using a step gradient from 15% EtOAc in hexanes to 20% EtOAc in hexanes). The purification affords 2-[5-(acetyloxy)-2,2-dimethyl-3,4-dihydro-2H-benzo[h]chromen-6-yl] 1-tert-butyl (2S)-pyrrolidine-1,2-dicarboxylate (11) (1.22 g) and 2-[6-(acetyloxy)-2,2-dimethyl-3,4-dihydro-2H-benzo[h]chromen-6-yl] 1-tert-butyl (2S)-pyrrolidine-1,2-dicarboxylate (12) (0.21 g) as a pure white solids (Combined yield: 24%). 2-[5-(acetyloxy)-2,2-dimethyl-3,4-dihydro-2H-benzo[h]chromen-6-yl] 1-tert-butyl (2S)-pyrrolidine-1,2-dicarboxylate (11): M.p.=83° C.; 400 MHz $^1$H NMR (CDCl$_3$) δ: 8.18 (d, J=8.4 Hz, 1H), 7.9-7.7 (m, 1H), 7.43 (m, 2H), 4.70 (d, J=8.8 Hz, 1H), 3.65-3.56 (m, 2H), 3.5-3.45 (m, 1H), 2.71-2.60 (m, 2H), 2.5-2.2 (m, 1H), 2.41 (s, 3H), 2.05-2.00 (m, 2H), 2.0-1.85 (m, 2H), 1.50 (s, 9H), 1.41 (m, 6H); LCMS: 484 [M+H]; Calc. for C$_{27}$H$_{33}$NO$_7$: C, 67.00; H, 6.88; N, 2.90; Found C, 67.14; H, 6.78; N, 2.85. 2-[6-(acetyloxy)-2,2-dimethyl-3,4-dihydro-2H-benzo[h]chromen-6-yl] 1-tert-butyl (2S)-pyrrolidine-1,2-dicarboxylate (12): M.p.=84° C.; 400 MHz $^1$H NMR (CDCl$_3$) δ: 8.19 (d, J=6.8 Hz, 1H), 7.7-7.6 (m, 1H), 7.44 (m, 2H), 4.63 (m, 1H), 3.65-3.56 (m, 2H), 3.5-3.4 (m, 1H), 2.73-2.67 (m, 2H), 2.5-2.2 (m, 1H), 2.47 (s, 3H), 2.1-1.95 (m, 2H), 1.86 (t, J=6.6 Hz, 2H), 1.48 (s, 9H), 1.43-1.40 (m, 6H); LCMS: 484 [M+H]; Calc. for C$_{27}$H$_{33}$NO$_7$: C, 67.00; H, 6.88; N, 2.90; Found C, 67.32; H, 6.58; N, 2.84.

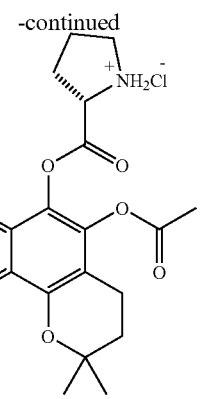

5-(acetyloxy)-2,2-dimethyl-3,4-dihydro-2H-benzo[h]chromen-6-yl L-prolinate hydrochloride (13—Prodrug 5). To a solution of 2-[5-(acetyloxy)-2,2-dimethyl-3,4-dihydro-2H-benzo[h]chromen-6-yl] 1-tert-butyl (2S)-pyrrolidine-1,2-dicarboxylate (11) (1.2 g, 2.5 mmol) in 1,4-dioxane (5 mL) is added a solution of hydrogen chloride gas in anhydrous 1,4-dioxane (4.0 M, 10 mL). The reaction is stirred at room temperature for 4 hours. The reaction is dried under reduced pressure. The desired product is obtained as a white solid (1.015 g, 93%) M.p.=125-130° C.; 400 MHz $^1$H NMR (CDCl$_3$) δ: 8.81 (br. s, 2H), 8.18 (d, J=8.8 Hz, 1H), 7.65 (d, J=7.6 Hz, 1H), 7.44 (m, 2H), 4.81 (br. s, 1H), 3.8-3.6 (m, 1H), 3.46 (br. s, 2H), 2.65-2.5 (m, 1H), 2.57 (t, J=6.4 Hz, 2H), 2.4-2.3 (m, 1H), 2.38 (s, 3H), 2.15-2.00 (m, 2H), 1.85-1.70 (m, 1H), 1.77 (t, J=6.4 Hz, 2H), 1.36 (s, 3H), 1.35 (s, 3H); LCMS: 384 [M+H]; Calc. for C$_{22}$H$_{25}$NO$_5$.1.58 HCl: C, 59.86; H, 6.07; N, 3.18; Found C, 59.91; H, 6.09; N, 2.91.

I. Example 9

Synthesis of 6-(acetyloxy)-2,2-dimethyl-3,4-dihydro-2H-benzo[h]chromen-5-yl L-prolinate hydrochloride (14)

H. Example 8

Synthesis of 5-(acetyloxy)-2,2-dimethyl-3,4-dihydro-2H-benzo[h]chromen-6-yl L-prolinate hydrochloride (13)

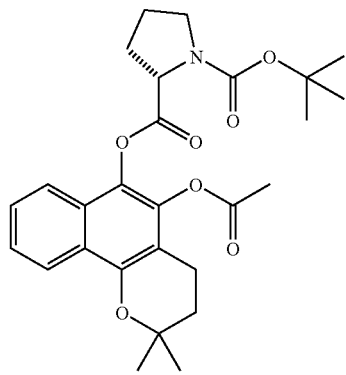

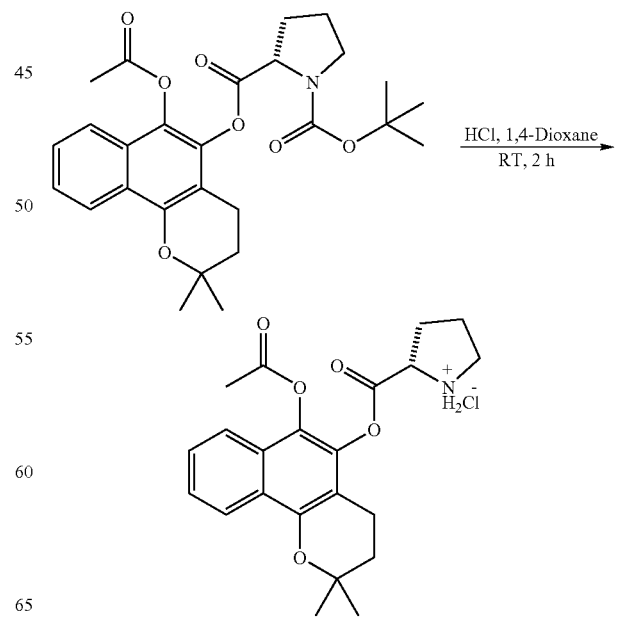

6-(acetyloxy)-2,2-dimethyl-3,4-dihydro-2H-benzo[h] chromen-5-yl L-prolinate hydrochloride (14). To a solution of 2-[6-(acetyloxy)-2,2-dimethyl-3,4-dihydro-2H-benzo[h] chromen-6-yl] 1-tert-butyl (2S)-pyrrolidine-1,2-dicarboxylate (12) (0.215 g, 0.45 mmol) in 1,4-dioxane (5.0 mL) is added a solution of hydrogen chloride gas in anhydrous 1,4-dioxane (4.0 M, 5 mL). The reaction is stirred at room temperature for 2 hours. The reaction is dried under reduced pressure. The desired product is obtained as a white solid (0.152 g, 77%) M.p.=100-110° C.; 400 MHz $^1$H NMR (CDCl$_3$) δ: 8.21 (d, J=9.2 Hz, 1H), 7.63 (d, J=7.2 Hz, 1H), 7.46 (m, 2H), 4.76 (br. s, 1H), 3.85-3.4 (m, 3H), 2.66 (m, 2H), 2.42 (m, 3H), 2.17 (m, 2H), 1.84 (m, 2H), 1.48 (m, 2H), 1.39 (s, 6H); LCMS: 384 [M+H]; Calc. for $C_{22}H_{25}NO_5 \cdot 1.78$ HCl: C, 58.88; H, 6.02; N, 3.12; Found C, 58.96; H, 6.17; N, 2.84.

J. Example 10

Synthesis of 4-[5-(acetyloxy)-2,2-dimethyl-3,4-dihydro-2H-benzo[h]chromen-6-yl] 1-tert-butyl piperidine-1,4-dicarboxylate (15) and 4-[6-(acetyloxy)-2,2-dimethyl-3,4-dihydro-2H-benzo[h]chromen-5-yl] 1-tert-butyl piperidine-1,4-dicarboxylate (16)

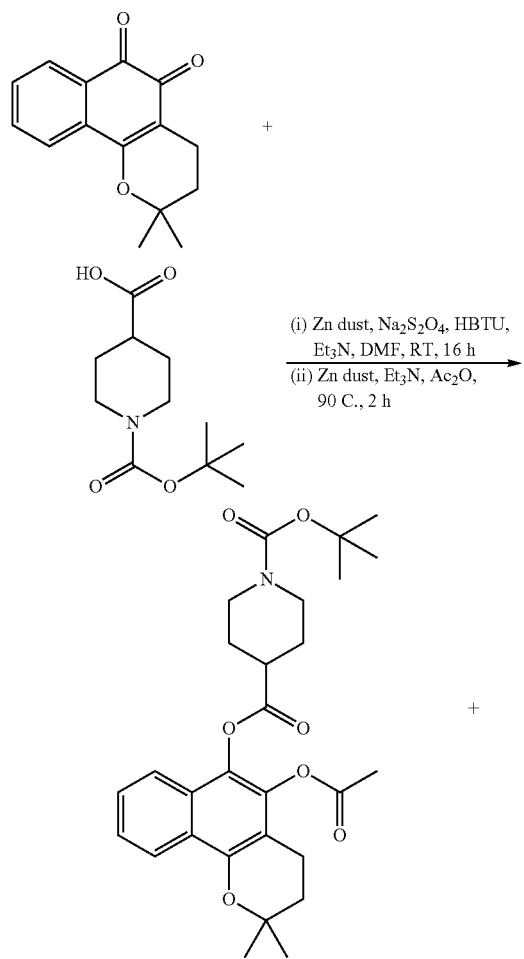

(i) Zn dust, Na$_2$S$_2$O$_4$, HBTU, Et$_3$N, DMF, RT, 16 h
(ii) Zn dust, Et$_3$N, Ac$_2$O, 90 C., 2 h

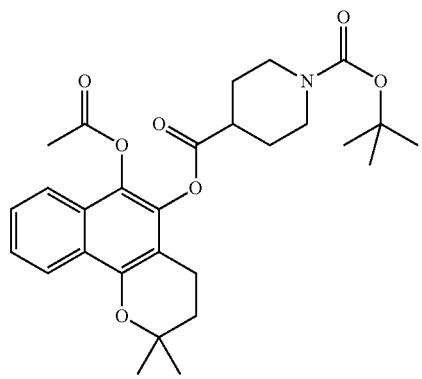

4-[5-(acetyloxy)-2,2-dimethyl-3,4-dihydro-2H-benzo[h]chromen-6-yl] 1-tert-butyl piperidine-1,4-dicarboxylate (15) and 4-[6-(acetyloxy)-2,2-dimethyl-3,4-dihydro-2H-benzo[h]chromen-5-yl] 1-tert-butyl piperidine-1,4-dicarboxylate (16). The compounds 4-[5-(acetyloxy)-2,2-dimethyl-3,4-dihydro-2H-benzo[h]chromen-6-yl] 1-tert-butyl piperidine-1,4-dicarboxylate (15) and 4-[6-(acetyloxy)-2,2-dimethyl-3,4-dihydro-2H-benzo[h]chromen-5-yl] 1-tert-butyl piperidine-1,4-dicarboxylate (16) are synthesized as described in example 1 using zinc dust (4.0 g, 61.2 mmol), 2,2-dimethyl-3,4-dihydro-2H-benzo[h]chromene-5,6-dione (4.0 g, 16.5 mmol), Na$_2$S$_2$O$_4$ (11.7 g, 66.1 mmol), 1-(tert-butoxycarbonyl)piperidine-4-carboxylic acid (9.46 g, 41.3 mmol), triethylamine (2.6 mL, 18.2 mmol), HBTU (15.7 g, 41.3 mmol) and DMF (100 mL) for the 1$^{st}$ step. The acetylation step is carried out using zinc dust (2.0 g, 30.6 mmol), thriethylamine (2.6 mL, 18.2 mmol) and acetic anhydride (40 mL). Both the compounds are generated in the reaction. The crude mixture is purified by flash column chromatography (SiO$_2$, step gradient from 100% dichloromethane to 2% EtOAc in dichloromethane) to afford pure desired product (3.2 g, 39%) as mixture of isomers (15:16) in a ratio of 3:1 as established by $^1$H NMR. Mixture of two isomers, ratio by NMR=3:1. M.p.=75-78° C.; 400 MHz $^1$H NMR (CDCl$_3$), major isomer δ: 8.21 (d, J=7.6 Hz, 1H), 7.61 (d, J=7.6 Hz, 1H), 7.45 (m, 2H), 4.13 (m, 2H), 3.0-2.8 (m, 3H), 2.67 (t, J=6.8 Hz, 2H), 2.34 (s, 3H), 2.2-2.0 (m, 2H), 1.95-1.8 (m, 4H), 1.48 (s, 9H), 1.42 (s, 6H); minor isomer δ: 8.21 (d, J=7.6 Hz, 1H), 7.61 (d, J=8.0 Hz, 1H), 7.45 (m, 2H), 4.13 (m, 2H), 3.0-2.8 (m, 3H), 2.64 (t, J=7.6 Hz, 2H), 2.41 (s, 3H), 2.2-2.0 (m, 2H), 1.95-1.8 (m, 4H), 1.48 (s, 9H), 1.42 (s, 6H); LCMS: 498 [M+H]; Calc. for $C_{28}H_{35}NO_7$: C 67.53, H 7.09, N 2.81; Found C, 67.30; H, 6.81; N, 2.76.

K. Example 11

Synthesis of 5-(acetyloxy)-2,2-dimethyl-3,4-dihydro-2H-benzo[h]chromen-6-yl piperidine-4-carboxylate hydrochloride (17) and 6-(acetyloxy)-2,2-dimethyl-3,4-dihydro-2H-benzo[h]chromen-5-yl piperidine-4-carboxylate hydrochloride (18)

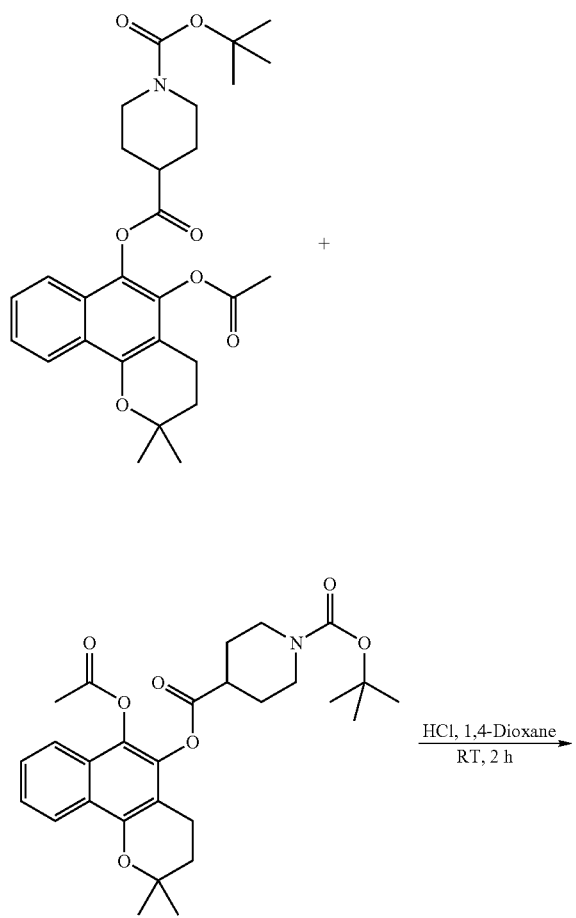

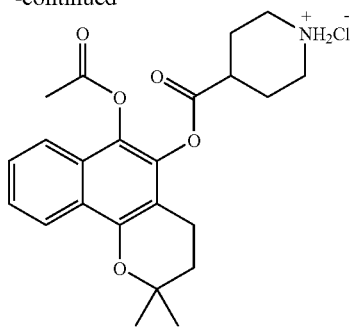

5-(acetyloxy)-2,2-dimethyl-3,4-dihydro-2H-benzo[h]chromen-6-yl piperidine-4-carboxylate hydrochloride (17) and 6-(acetyloxy)-2,2-dimethyl-3,4-dihydro-2H-benzo[h]chromen-5-yl piperidine-4-carboxylate hydrochloride (18). To a solution of 4-[5-(acetyloxy)-2,2-dimethyl-3,4-dihydro-2H-benzo[h]chromen-6-yl] 1-tert-butyl piperidine-1,4-dicarboxylate (15) and 4-[6-(acetyloxy)-2,2-dimethyl-3,4-dihydro-2H-benzo[h]chromen-5-yl] 1-tert-butyl piperidine-1,4-dicarboxylate (16) (1.586 g, 3.18 mmol) in 1,4-dioxane (10 mL) is added a solution of hydrogen chloride gas in anhydrous 1,4-dioxane (4.0 M, 20 mL). The reaction is stirred at room temperature for 2 hours. The reaction is dried under reduced pressure. The product is obtained as a white solid (1.31 g, 94%) and is a mixture of both the isomers 5-(acetyloxy)-2,2-dimethyl-3,4-dihydro-2H-benzo[h]chromen-6-yl piperidine-4-carboxylate hydrochloride (17) and 6-(acetyloxy)-2,2-dimethyl-3,4-dihydro-2H-benzo[h]chromen-5-yl piperidine-4-carboxylate hydrochloride (18). The ratio of the isomers 17:18 is determined to be 3:1 by $^1$H NMR. Mixture of two isomers, ratio by NMR=3:1. M.p.=225-229° C.; 400 MHz $^1$H NMR (DMSO-$d_6$), major isomer δ: 8.87 (br. s, 2H), 8.12 (d, J=7.6 Hz, 1H), 7.69 (d, J=8.0 Hz, 1H), 7.50 (m, 2H), 3.4-3.3 (m, 1H), 3.21 (tt, J=11.4, 3.8 Hz, 2H), 3.02 (m, 2H), 2.65-2.55 (m, 2H), 2.37 (s, 3H), 2.3-2.15 (m, 2H), 2.0-1.9 (m, 2H), 1.87 (t, J=6.6 Hz, 2H), 1.38 (s, 6H); minor isomer δ: 8.87 (br. s, 2H), 8.12 (d, J=7.6 Hz, 1H), 7.77 (d, J=7.2 Hz, 1H), 7.50 (m, 2H), 3.4-3.3 (m, 1H), 3.12 (tt, J=11.3, 3.8 Hz, 2H), 3.02 (m, 2H), 2.65-2.55 (m, 2H), 2.43 (s, 3H), 2.3-2.15 (m, 2H), 2.0-1.9 (m, 2H), 1.87 (t, J=6.6 Hz, 2H), 1.38 (s, 6H); LCMS: 398 [M+H]; Calc. for $C_{23}H_{27}NO_5 \cdot 1.12$ HCl: C 62.97, H 6.47, N 3.20; Found C, 63.04; H, 6.71; N, 3.23.

L. Example 12

Synthesis of 5-(acetyloxy)-2,2-dimethyl-3,4-dihydro-2H-benzo[h]chromen-6-yl isonicotinate hydrochloride (19) and 6-(acetyloxy)-2,2-dimethyl-3,4-dihydro-2H-benzo[h]chromen-5-yl isonicotinate hydrochloride (20)

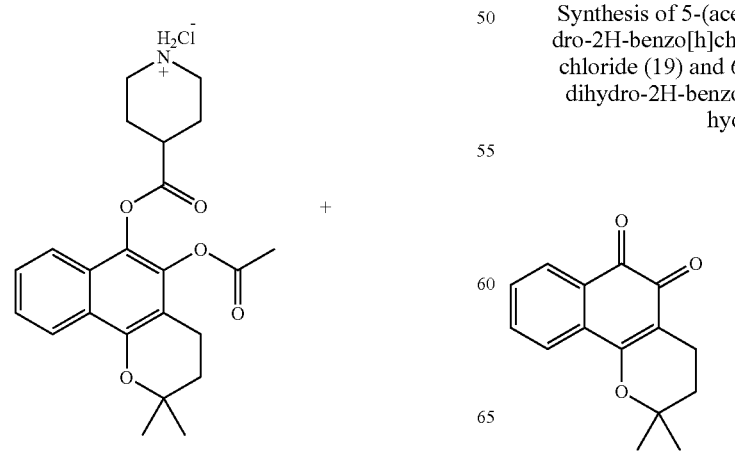

-continued

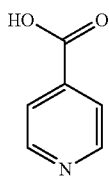
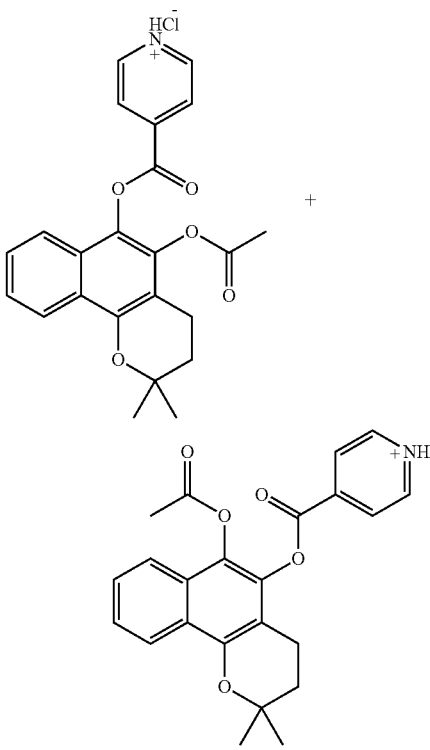

5-(acetyloxy)-2,2-dimethyl-3,4-dihydro-2H-benzo[h]chromen-6-yl isonicotinate hydrochloride (19) and 6-(acetyloxy)-2,2-dimethyl-3,4-dihydro-2H-benzo[h]chromen-5-yl isonicotinate hydrochloride (20). The compounds 5-(acetyloxy)-2,2-dimethyl-3,4-dihydro-2H-benzo[h]chromen-6-yl isonicotinate hydrochloride (19) and 6-(acetyloxy)-2,2-dimethyl-3,4-dihydro-2H-benzo[h]chromen-5-yl isonicotinate hydrochloride (20) are synthesized as described in example 1 using zinc dust (1.5 g, 22.9 mmol), 2,2-dimethyl-3,4-dihydro-2H-benzo[h]chromene-5,6-dione (1.5 g, 6.2 mmol), $Na_2S_2O_4$ (4.32 g, 24.77 mmol), isonicotinic acid (1.52 g, 12.4 mmol), triethylamine (0.78 mL, 5.57 mmol), HBTU (4.7 g, 12.38 mmol) and DMF (15 mL) for the $1^{st}$ step. The acetylation step is carried out using zinc dust (0.75 g, 11.5 mmol), thriethylamine (0.9 mL, 6.4 mmol) and acetic anhydride (10 mL). Both the compounds are generated in the reaction. The crude mixture is purified by flash column chromatography ($SiO_2$, using a gradient from 100% dichloromethane to 5% EtOAc in dichloromethane) to afford pure desired free-base of the product (1.038 g) as mixture of isomers. The free-base of the product is dissolved in $Et_2O$ and treated with a solution of hydrogen chloride gas in anhydrous 1,4-dioxane (4.0 M, 1.2 mL) for 15 minutes at room temperature. The desired hydrogen chloride salt of the product separates out as a pale yellow solid (0.973 g, 36%), which is filtered and dried under reduced pressure. The desired product is a mixture of isomers (19:20) and the ratio is determined to be 4:1 by $^1H$ NMR. Mixture of two isomers, ratio by NMR=4:1. M.p.=228-232° C.; 400 MHz $^1H$ NMR (DMSO-$d_6$), major isomer δ: 9.05-8.95 (m, 2H), 8.2-8.15 (m, 2H), 8.12 (m, 1H), 7.85-7.75 (m, 1H), 7.62-7.50 (m, 2H), 2.67 (t, J=6.8 Hz, 2H), 2.22 (s, 3H), 1.90 (t, J=6.6 Hz, 2H), 1.41 (s, 6H); minor isomer δ: 9.05-8.95 (m, 2H), 8.2-8.15 (m, 2H), 8.12 (m, 1H), 7.85-7.75 (m, 1H), 7.62-7.50 (m, 2H), 2.67 (t, J=6.8 Hz, 2H), 2.29 (s, 3H), 1.88 (t, J=6.8 Hz, 2H), 1.41 (s, 6H); LCMS: 392 [M+H]; Calc. for $C_{23}H_{21}NO_5 \cdot 1.21$ HCl: C 63.37, H 5.14, N 3.22; Found C, 63.41; H, 5.36; N, 3.16.

M. Example 13

Synthesis of 5-(acetyloxy)-2,2-dimethyl-3,4-dihydro-2H-benzo[h]chromen-6-yl nicotinate hydrochloride (21) and 6-(acetyloxy)-2,2-dimethyl-3,4-dihydro-2H-benzo[h]chromen-5-yl nicotinate hydrochloride (22)

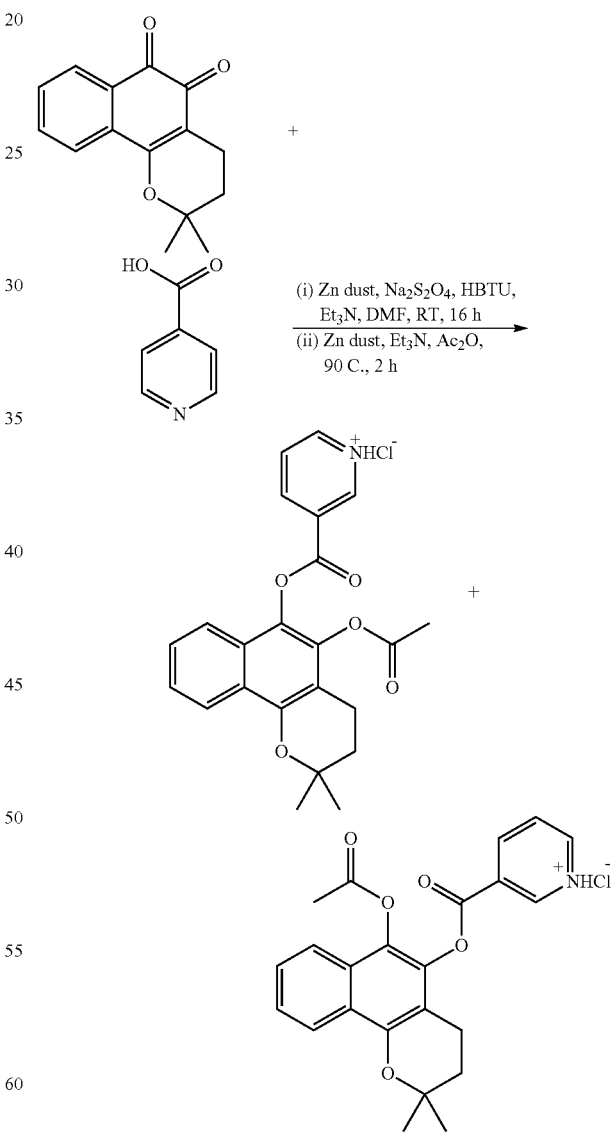

5-(acetyloxy)-2,2-dimethyl-3,4-dihydro-2H-benzo[h]chromen-6-yl nicotinate hydrochloride (21—Prodrug 9) and 6-(acetyloxy)-2,2-dimethyl-3,4-dihydro-2H-benzo[h]chromen-5-yl nicotinate hydrochloride (22). The compounds 5-(acetyloxy)-2,2-dimethyl-3,4-dihydro-2H-benzo[h]chromen-6-yl nicotinate hydrochloride (21) and 6-(acetyloxy)-2,2-dimethyl-3,4-dihydro-2H-benzo[h]chromen-5-yl nicotinate hydrochloride (22) are synthesized as described in example 1 using zinc dust (1.5 g, 22.9 mmol), 2,2-dimethyl-3,4-dihydro-2H-benzo[h]chromene-5,6-dione (1.5 g, 6.2 mmol), $Na_2S_2O_4$ (4.32 g, 24.77 mmol), nicotinic acid (1.52 g, 12.4 mmol), triethylamine (0.78 mL, 5.57 mmol), HBTU (4.7 g, 12.38 mmol) and DMF (15 mL) for the $1^{st}$ step. The acetylation step is carried out using zinc dust (0.75 g, 11.5 mmol), thriethylamine (0.9 mL, 6.4 mmol) and acetic anhydride (10 mL). Both the compounds are generated in the reaction. The crude mixture is purified by flash column chromatography ($SiO_2$, using a gradient from 100% dichloromethane to 5% EtOAc in dichloromethane) to afford pure desired free-base of the product (1.184 g) as mixture of isomers. The free-base of the product is dissolved in $Et_2O$ and treated with a solution of hydrogen chloride gas in anhydrous 1,4-dioxane (4.0 M, 1.2 mL) for 15 minutes at room temperature. The desired hydrogen chloride salt of the product is separated out as a pale yellow solid (1.123 g, 41%), which is filtered and dried under reduced pressure. The desired product is a mixture of isomers (21:22) and the ratio is determined to be 3.3:1 by $^1H$ NMR. Mixture of two isomers, ratio by NMR=3.3:1. M.p.=214-218° C.; 400 MHz $^1H$ NMR (DMSO-$d_6$), major isomer δ: 9.84 (d, J=2.0 Hz, 1H), 9.01-8.98 (m, 1H), 8.62-8.55 (m, 1H), 8.20-8.10 (m, 1H), 7.85-7.70 (m, 2H), 7.65-7.50 (m, 2H), 2.67 (t, J=6.6 Hz, 2H), 2.22 (s, 3H), 1.90 (t, J=6.4 Hz, 2H), 1.41 (s, 6H); minor isomer δ: 9.32 (d, J=2.4 Hz, 1H), 9.01-8.98 (m, 1H), 8.62-8.55 (m, 1H), 8.20-8.10 (m, 1H), 7.85-7.70 (m, 2H), 7.65-7.50 (m, 2H), 2.71 (t, J=6.4 Hz, 2H), 2.28 (s, 3H), 1.88 (t, J=6.8 Hz, 2H), 1.41 (s, 6H); LCMS: 392 [M+H]; Calc. for $C_{23}H_{21}NO_5 \cdot 1.4$ HCl: C, 62.38; H, 5.10; N, 3.17; Found C, 62.42; H, 5.01; N, 3.15.

N. Example 14

Synthesis of tert-butyl 4-(2-{[5-(acetyloxy)-2,2-dimethyl-3,4-dihydro-2H-benzo[h]chromen-6-yl]oxy}-2-oxoethyl)piperidine-1-carboxylate (23) and tert-butyl 4-(2-{[6-(acetyloxy)-2,2-dimethyl-3,4-dihydro-2H-benzo[h]chromen-5-yl]oxy}-2-oxoethyl)piperidine-1-carboxylate (24)

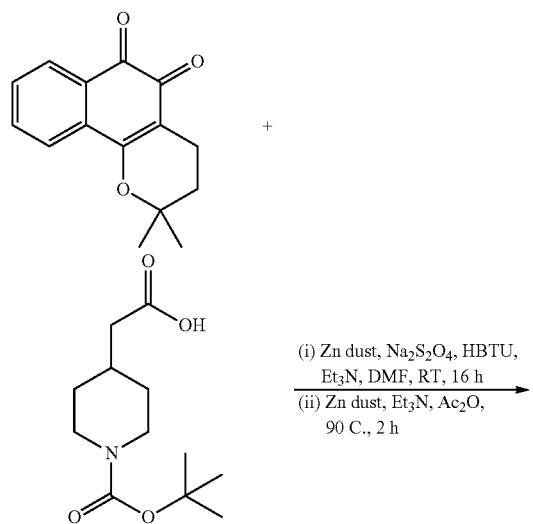

(i) Zn dust, $Na_2S_2O_4$, HBTU, $Et_3N$, DMF, RT, 16 h
(ii) Zn dust, $Et_3N$, $Ac_2O$, 90 C., 2 h

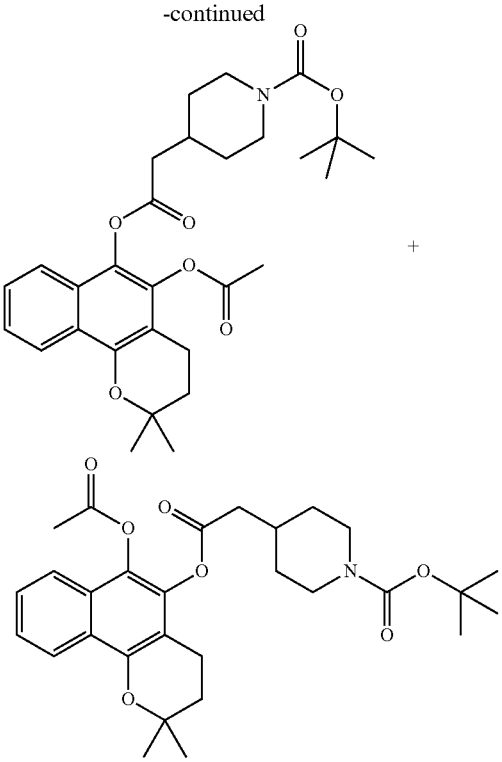

tert-butyl 4-(2-{[5-(acetyloxy)-2,2-dimethyl-3,4-dihydro-2H-benzo[h]chromen-6-yl]oxy}-2-oxoethyl)piperidine-1-carboxylate (23) and tert-butyl 4-(2-{[6-(acetyloxy)-2,2-dimethyl-3,4-dihydro-2H-benzo[h]chromen-5-yl]oxy}-2-oxoethyl)piperidine-1-carboxylate (24). The compounds tert-butyl 4-(2-{[5-(acetyloxy)-2,2-dimethyl-3,4-dihydro-2H-benzo[h]chromen-6-yl]oxy}-2-oxoethyl)piperidine-1-carboxylate (23) and tert-butyl 4-(2-{[6-(acetyloxy)-2,2-dimethyl-3,4-dihydro-2H-benzo[h]chromen-5-yl]oxy}-2-oxoethyl)piperidine-1-carboxylate (24) are synthesized as described in scheme 1a using zinc dust (2.0 g, 30.5 mmol), 2,2-dimethyl-3,4-dihydro-2H-benzo[h]chromene-5,6-dione (2.0 g, 8.3 mmol), $Na_2S_2O_4$ (5.8 g, 33.0 mmol), [1-(tert-butoxycarbonyl)piperidin-4-yl]acetic acid (2.36 g, 16.5 mmol), triethylamine (1.04 mL, 7.4 mmol), HBTU (6.26 g, 16.5 mmol) and DMF (20 mL) for the $1^{st}$ step. The acetylation step is carried out using zinc dust (1.0 g, 15.3 mmol), thriethylamine (1.2 mL, 8.3 mmol) and acetic anhydride (15 mL). Both the compounds are generated in the reaction. The crude mixture is purified using two consecutive flash column chromatography ($SiO_2$, $1^{st}$ purification is carried out using linear gradient from 50% dichloromethane in hexanes to 100% dichloromethane. $2^{nd}$ purification using 2% EtOAc in dichloromethane) to afford pure desired product (1.42 g, 33%) as mixture of isomers (23:24) in a ratio of 2.7:1 as established by $^1H$ NMR. Mixture of two isomers, ratio by NMR=2.7:1. M.p.=70-72° C.; 400. MHz $^1H$ NMR ($CDCl_3$), major isomer δ: 8.21 (d, J=8.0 Hz, 1H), 7.63 (d, J=7.8 Hz, 1H), 7.50-7.40 (m, 2H), 4.10-4.00 (m, 2H), 2.78 (m, 2H), 2.70-2.60 (m, 4H), 2.34 (s, 3H), 2.20-2.05 (m, 1H), 1.87 (t, J=6.8 Hz, 2H), 1.90-1.80 (m, 2H), 1.47 (s, 9H), 1.42 (s, 6H), 1.35-1.20 (m, 2H); minor isomer δ: 8.20 (d, J=7.6 Hz, 1H), 7.67 (d, J=7.6 Hz, 1H), 7.50-7.40 (m, 2H), 4.10-4.00 (m, 2H), 2.78 (m, 2H), 2.70-2.60 (m, 4H), 2.41 (s, 3H), 2.20-2.05 (m, 1H), 1.87 (t, J=6.8 Hz, 2H), 1.90-1.80 (m, 2H), 1.47 (s, 9H), 1.42 (s, 6H), 1.35-1.20 (m, 2H); LCMS: 512 [M+H]; Calc. for C$_{29}$H$_{37}$NO$_7$: C, 68.02; H, 7.29; N, 2.74; Found C, 68.09; H, 6.94; N, 2.70.

O. Example 15

Synthesis of 5-(acetyloxy)-2,2-dimethyl-3,4-dihydro-2H-benzo[h]chromen-6-yl piperidin-4-ylacetate hydrochloride (25) and 6-(acetyloxy)-2,2-dimethyl-3,4-dihydro-2H-benzo[h]chromen-5-yl piperidin-4-ylacetate hydrochloride (26)

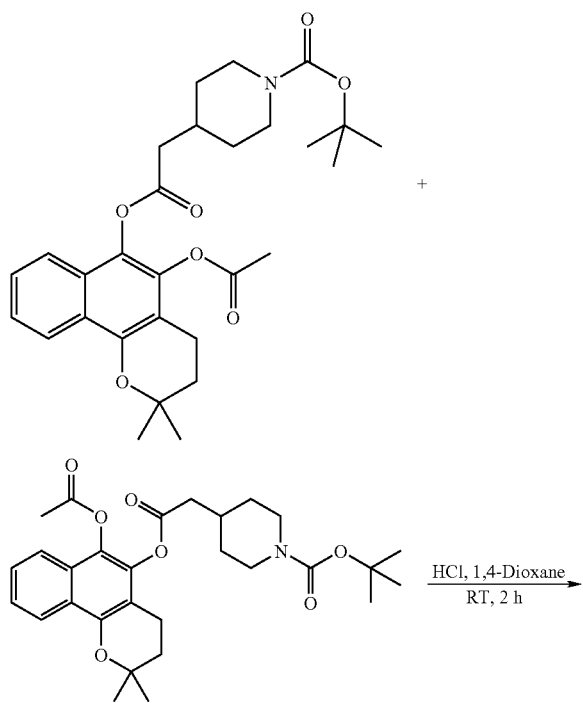

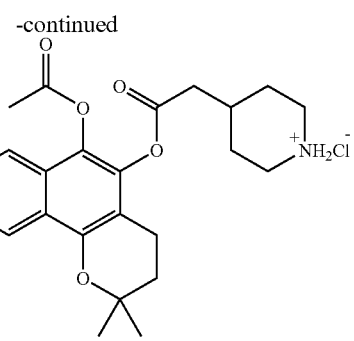

5-(acetyloxy)-2,2-dimethyl-3,4-dihydro-2H-benzo[h]chromen-6-yl piperidin-4-ylacetate hydrochloride (25—Prodrug 7) and 6-(acetyloxy)-2,2-dimethyl-3,4-dihydro-2H-benzo[h]chromen-5-yl piperidin-4-ylacetate hydrochloride (26). To a solution of tert-butyl 4-(2-{[5-(acetyloxy)-2,2-dimethyl-3,4-dihydro-2H-benzo[h]chromen-6-yl]oxy}-2-oxoethyl)piperidine-1-carboxylate (23) and tert-butyl 4-(2-{[6-(acetyloxy)-2,2-dimethyl-3,4-dihydro-2H-benzo[h]chromen-5-yl]oxy}-2-oxoethyl)piperidine-1-carboxylate (24) (1.36 g, 2.66 mmol) in 1,4-dioxane (10 mL) is added a solution of hydrogen chloride gas in anhydrous 1,4-dioxane (4.0 M, 20 mL). The reaction is stirred at room temperature for 30 minutes. The reaction is dried under reduced pressure. The product is obtained as a white solid (1.09 g, 92%) and is a mixture of both the isomers 5-(acetyloxy)-2,2-dimethyl-3,4-dihydro-2H-benzo[h]chromen-6-yl piperidin-4-ylacetate hydrochloride (25) and 6-(acetyloxy)-2,2-dimethyl-3,4-dihydro-2H-benzo[h]chromen-5-yl piperidin-4-ylacetate hydrochloride (26). The ratio of the isomers 25:26 is determined to be 2.6:1 by $^1$H NMR. Mixture of two isomers, ratio by NMR=2.6:1. M.p.=207-210° C.; 400 MHz $^1$H NMR (DMSO-d$_6$), major isomer δ: 9.02 (br. s, 2H), 8.10 (d, J=7.2 Hz, 1H), 7.70 (d, J=8.0 Hz, 1H), 7.60-7.45 (m, 2H), 3.27 (d, J=12.8 Hz, 2H), 2.91 (t, J=12.6 Hz, 2H), 2.79 (d, J=6.8 Hz, 2H), 2.60 (t, J=6.4 Hz, 2H), 2.35 (s, 3H), 2.20-2.05 (m, 1H), 1.95-1.80 (m, 4H), 1.60-1.45 (m, 2H), 1.37 (s, 6H); minor isomer δ: 9.02 (br. s, 2H), 8.10 (d, J=7.2 Hz, 1H), 7.75 (d, J=7.6 Hz, 1H), 7.60-7.45 (m, 2H), 3.27 (d, J=12.8 Hz, 2H), 2.91 (t, J=12.6 Hz, 2H), 2.69 (d, J=6.8 Hz, 2H), 2.60 (t, J=6.4 Hz, 2H), 2.41 (s, 3H), 2.20-2.05 (m, 1H), 1.95-1.80 (m, 4H), 1.60-1.45 (m, 2H), 1.37 (s, 6H); LCMS: 412 [M+H]; Calc. for C$_{24}$H$_{29}$NO$_5$·1.3 HCl: C, 62.76; H, 6.65; N, 3.05; Found C, 62.58; H, 6.78; N, 3.02.

P. Example 16

Synthesis of 5-(acetyloxy)-2,2-dimethyl-3,4-dihydro-2H-benzo[h]chromen-6-yl N-(tert-butoxycarbonyl)-2-methylalaninate (27)

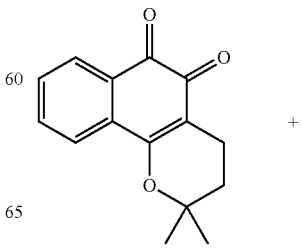

Q. Example 17

Synthesis of 5-(acetyloxy)-2,2-dimethyl-3,4-dihydro-2H-benzo[h]chromen-6-yl 2-methylalaninate hydrochloride (28)

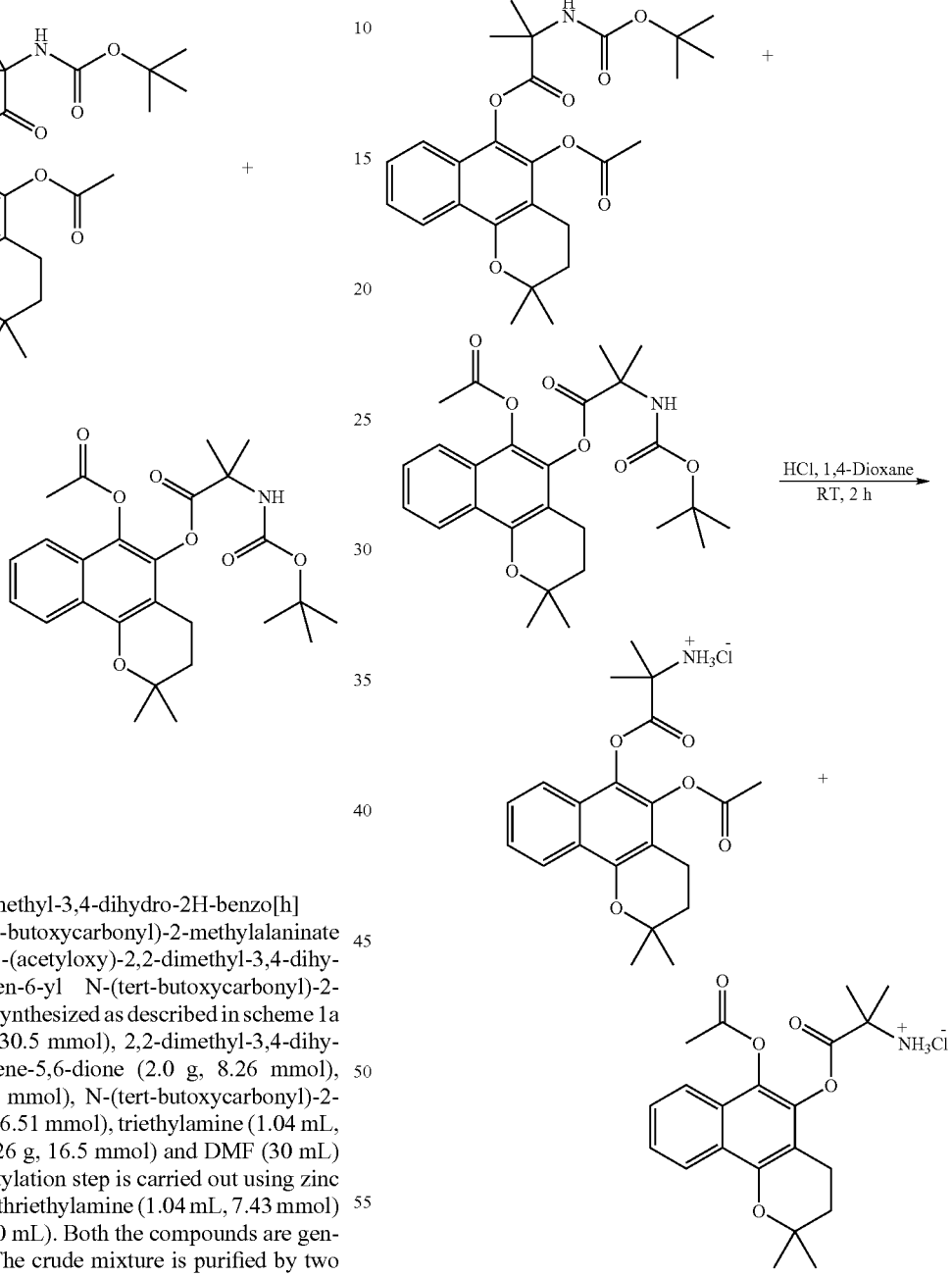

5-(acetyloxy)-2,2-dimethyl-3,4-dihydro-2H-benzo[h]chromen-6-yl N-(tert-butoxycarbonyl)-2-methylalaninate (27). The compound 5-(acetyloxy)-2,2-dimethyl-3,4-dihydro-2H-benzo[h]chromen-6-yl N-(tert-butoxycarbonyl)-2-methylalaninate (27) is synthesized as described in scheme 1a using zinc dust (2.0 g, 30.5 mmol), 2,2-dimethyl-3,4-dihydro-2H-benzo[h]chromene-5,6-dione (2.0 g, 8.26 mmol), $Na_2S_2O_4$ (5.75 g, 33.0 mmol), N-(tert-butoxycarbonyl)-2-methylalanine (3.36 g, 16.51 mmol), triethylamine (1.04 mL, 7.43 mmol), HBTU (6.26 g, 16.5 mmol) and DMF (30 mL) for the $1^{st}$ step. The acetylation step is carried out using zinc dust (1.0 g, 15.3 mmol), thriethylamine (1.04 mL, 7.43 mmol) and acetic anhydride (20 mL). Both the compounds are generated in the reaction. The crude mixture is purified by two consecutive flash column chromatography ($SiO_2$, $1^{st}$ using a gradient from 100% dichloromethane to 2% EtOAc in dichloromethane and $2^{nd}$ using a gradient from 10% EtOAc in hexanes to 25% EtOAc in hexanes) to afford pure desired single isomer product (0.405 g, %) as a white solid. 400 MHz $^1H$ NMR ($CDCl_3$) δ: 8.19 (d, J=8.8 Hz, 1H), 7.85 (d, J=7.6 Hz, 1H), 7.50-7.35 (m, 2H), 5.19 (br. s, 1H), 2.67 (t, J=6.6 Hz, 2H), 2.37 (s, 3H), 1.87 (t, J=6.8 Hz, 2H), 1.78 (s, 6H), 1.47 (s, 9H), 1.42 (s, 6H); LCMS: 472 [M+H].

5-(acetyloxy)-2,2-dimethyl-3,4-dihydro-2H-benzo[h]chromen-6-yl 2-methylalaninate hydrochloride (28). To a solution of 5-(acetyloxy)-2,2-dimethyl-3,4-dihydro-2H-benzo[h]chromen-6-yl N-(tert-butoxycarbonyl)-2-methylalaninate (27) (0.4 g, 0.85 mmol) in 1,4-dioxane (5 mL) is added a solution of hydrogen chloride gas in anhydrous 1,4-dioxane (4.0 M, 10 mL). The reaction is stirred at room temperature for 2 hours. The reaction is dried under reduced pressure and the resulting solid is triturated with Et$_2$O to afford the desired product as a white solid (0.388 g, 97%). M.p.=283-284° C.; 400 MHz $^1$H NMR (DMSO-d$_6$) δ: 8.93 (br. s, 3H), 8.15 (d, J=8.4 Hz, 1H), 7.72 (d, J=8.0 Hz, 1H), 7.65-7.50 (m, 2H), 2.63 (t, J=6.6 Hz, 2H), 2.38 (s, 3H), 1.89 (t, J=6.6 Hz, 2H), 1.78 (s, 6H), 1.39 (s, 6H); LCMS: 372 [M+H]; Calc. for C$_{21}$H$_{25}$NO$_5$.1.15HCl: C, 60.96; H, 6.38; N, 3.39; Found C, 61.01; H, 6.06; N, 3.30.

R. Example 18

Synthesis of 5-(acetyloxy)-2,2-dimethyl-3,4-dihydro-2H-benzo[h]chromen-6-yl N-(tert-butoxycarbonyl)-β-alaninate (29) and 6-(acetyloxy)-2,2-dimethyl-3,4-dihydro-2H-benzo[h]chromen-5-yl N-(tert-butoxycarbonyl)-β-alaninate (30)

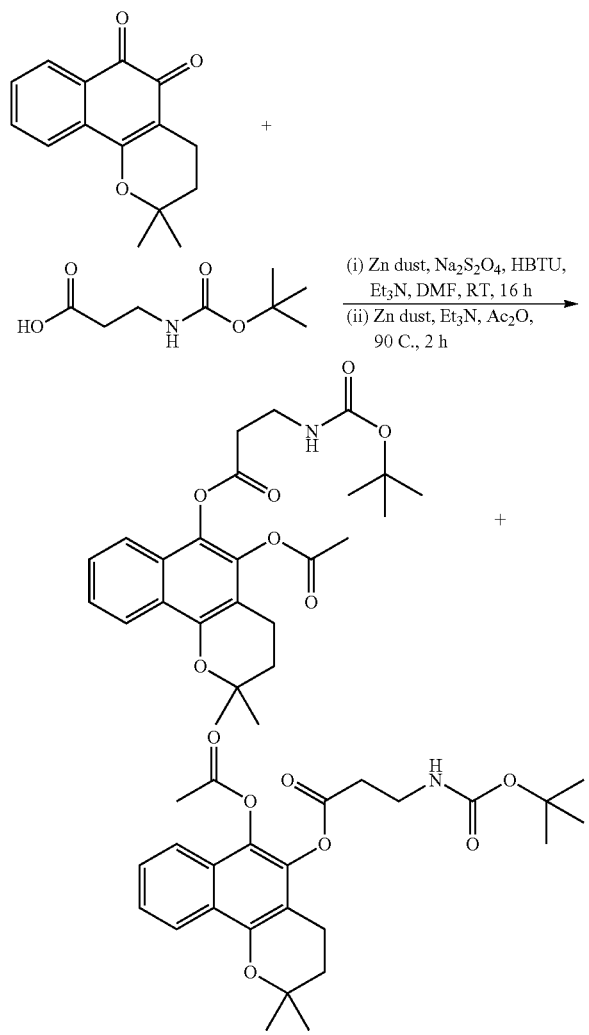

5-(acetyloxy)-2,2-dimethyl-3,4-dihydro-2H-benzo[h]chromen-6-yl N-(tert-butoxycarbonyl)-β-alaninate (29) and 6-(acetyloxy)-2,2-dimethyl-3,4-dihydro-2H-benzo[h]chromen-5-yl N-(tert-butoxycarbonyl)-β-alaninate (30). The compounds 5-(acetyloxy)-2,2-dimethyl-3,4-dihydro-2H-benzo[h]chromen-6-yl N-(tert-butoxycarbonyl)-β-alaninate (29) and 6-(acetyloxy)-2,2-dimethyl-3,4-dihydro-2H-benzo[h]chromen-5-yl N-(tert-butoxycarbonyl)-β-alaninate (30) are synthesized as described in example 1 using zinc dust (2.0 g, 30.6 mmol), 2,2-dimethyl-3,4-dihydro-2H-benzo[h]chromene-5,6-dione (2.0 g, 8.26 mmol), Na$_2$S$_2$O$_4$ (5.75 g, 33.0 mmol), N-(tert-butoxycarbonyl)-β-alanine (3.12 g, 16.5 mmol), triethylamine (1.0 mL, 7.1 mmol), HBTU (6.2 g, 16.5 mmol) and DMF (30 mL) for the 1$^{st}$ step. The acetylation step is carried out using zinc dust (2.0 g, 30.6 mmol), thriethylamine (2.0 mL, 14.2 mmol) and acetic anhydride (30 mL). Both the compounds are generated in the reaction. The crude mixture is purified by three consecutive flash column chromatography on SiO$_2$ (twice using a gradient from 10% EtOAc in hexanes to 25% EtOAc in hexanes once using 100% dichloromethane) to afford pure desired product as mixture of isomers (29:30) in a ratio of 7:1 as established by $^1$H NMR. M.p.=171-172° C.; 400 MHz $^1$H NMR (CDCl$_3$) δ: 8.21 (d, J=8.8 Hz, 1H), 7.64 (d, J=8.0 Hz, 1H), 7.50-7.40 (m, 2H), 5.12 (br. s, 1H), 3.60-3.50 (m, 2H), 2.94 (t, J=6.0 Hz, 2H), 2.69 (t, J=6.6 Hz, 2H), 2.35 (s, 3H), 1.88 (t, J=6.8 Hz, 2H), 1.46 (s, 9H), 1.43 (s, 6H); LCMS: 458 [M+H]; Calc. for C$_{25}$H$_{31}$NO$_7$: C 65.57, H 6.83, N 3.06; Found C, 65.69; H, 6.23; N, 3.19.

S. Example 19

Synthesis of 5-(acetyloxy)-2,2-dimethyl-3,4-dihydro-2H-benzo[h]chromen-6-yl-β-alaninate hydrochloride (31) and 6-(acetyloxy)-2,2-dimethyl-3,4-dihydro-2H-benzo[h]chromen-5-yl-(3-alaninate hydrochloride (32)

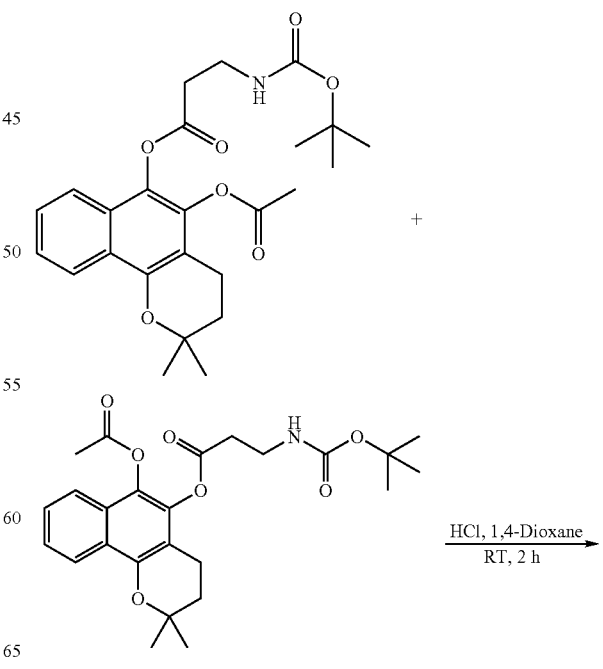

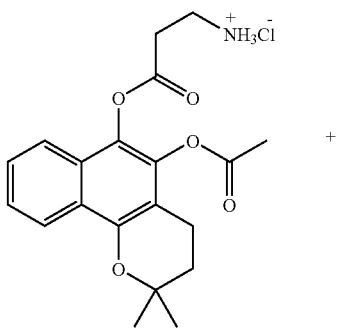

5-(acetyloxy)-2,2-dimethyl-3,4-dihydro-2H-benzo[h]chromen-6-yl-β-alaninate hydrochloride (31—Prodrug 8) and 6-(acetyloxy)-2,2-dimethyl-3,4-dihydro-2H-benzo[h]

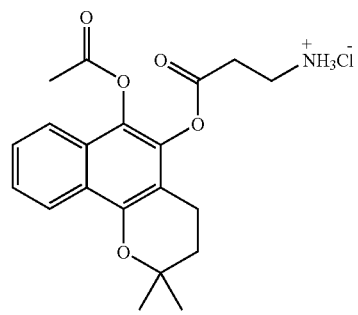

chromen-5-yl-β-alaninate hydrochloride (32). To a solution of 5-(acetyloxy)-2,2-dimethyl-3,4-dihydro-2H-benzo[h]chromen-6-yl N-(tert-butoxycarbonyl)-β-alaninate (29) and 6-(acetyloxy)-2,2-dimethyl-3,4-dihydro-2H-benzo[h]chromen-5-yl N-(tert-butoxycarbonyl)-β-alaninate (30) (1.0 g, 2.18 mmol) in 1,4-dioxane (5 mL) is added a solution of hydrogen chloride gas in anhydrous 1,4-dioxane (4.0 M, 5 mL). The reaction is stirred at room temperature for 16 hours. The reaction is dried under reduced pressure. The product is obtained as a white solid (0.55 g, 64%) after recrystallization in 30 of toluene and is a mixture of both the isomers 5-(acetyloxy)-2,2-dimethyl-3,4-dihydro-2H-benzo[h]chromen-6-yl-β-alaninate hydrochloride (31) and 6-(acetyloxy)-2,2-dimethyl-3,4-dihydro-2H-benzo[h]chromen-5-yl-β-alaninate hydrochloride (32). The ratio of the isomers 31:32 is determined to be 10:1 by $^1$H NMR. M.p.=173-176° C.; 400 MHz $^1$H NMR (DMSO-$d_6$) δ: 8.20-8.05 (m, 4H), 7.84 (d, J=7.6 Hz, 1H), 7.60-7.45 (m, 2H), 3.25-3.15 (m, 4H), 2.62 (t, J=6.6 Hz, 2H), 2.40 (s, 3H), 1.87 (t, J=6.6 Hz, 2H), 1.39 (s, 6H); LCMS: 387 [M+H]; Calc. for $C_{20}H_{23}NO_5 \cdot 1.38$ HCl: C, 58.86; H, 6.03; N, 3.43; Found C, 58.94; H, 5.67; N, 3.62.

T. Example 20

Synthesis of 5-Acetoxy-2,2-dimethyl-3,4-dihydro-2H-benzo[h]chromen-6-yloxycarbonylmethyl-ammonium: chloride 5-Acetoxy-2,2-dimethyl-3,4-dihydro-2H-benzo[h]chromen-6-yloxycarbonylmethyl-ammonium; chloride. A preferred β-lapachone prodrug composition of the invention using glycine as the amino acid moiety may be prepared in general accordance with Scheme Ia as follows.

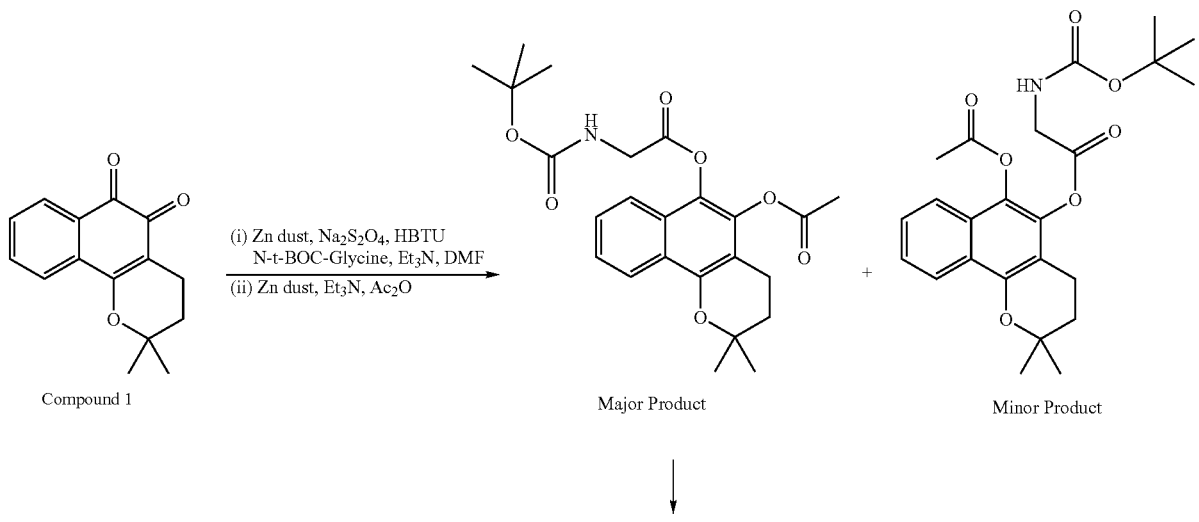

-continued

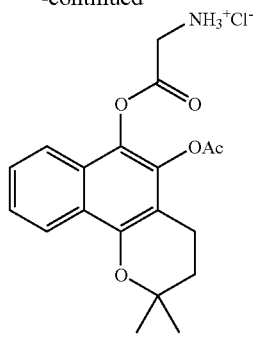

Prodrug 1

U. Example 21

Stability of β-Lapachone Prodrug Composition and Release of β-Lapachone

The release of β-lapachone from a β-lapachone prodrug composition of the invention may be demonstrated under basic conditions (1.0 N NaOH). For example, FIG. 1 shows the release of β-lapachone from Prodrug 1 at varying pH values.

What is claimed is:

1. A quinone prodrug composition comprising a quinone compound of formula I

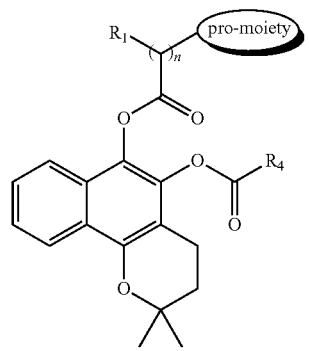
(I)

wherein
  $R_1$ is H or $C_1$-$C_4$ alkyl, optionally substituted with a sulfyl (—SH or thio alkyl) group;
  $R_4$ is $C_1$-$C_4$ alkyl, aryl or heteroaryl, wherein said aryl or heteroaryl is selected from the group consisting of phenyl, pyridyl, imidazole and thiazole, and is optionally substituted with one or more independently selected $C_1$-$C_3$ alkyl groups;
  the pro-moiety is selected from —($C_1$-$C_{11}$)alkyl, —($C_0$-$C_6$)alkyl-aryl, —($C_0$-$C_6$)alkyl-heteroaryl, —($C_0$-$C_6$) alkyl-aryl-heteroaryl, —($C_0$-$C_6$)alkyl-COOH, —($C_1$-$C_6$)alkyl-OH, 1-pyridyl, 2-pyridyl, 3-pyridyl, 4-pyridyl, aryl-heteroaryl,

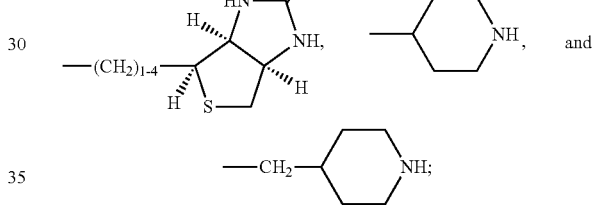

and n is 0, 1, 2 or 3, with the proviso that when n is 0, $R_1$ is not present.

2. The quinone prodrug composition of claim 1, wherein the quinone compound is β-lapachone.

3. A quinone prodrug composition, wherein the composition is a compound selected from the group consisting of

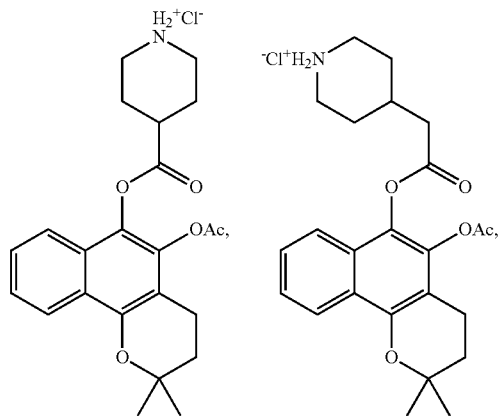

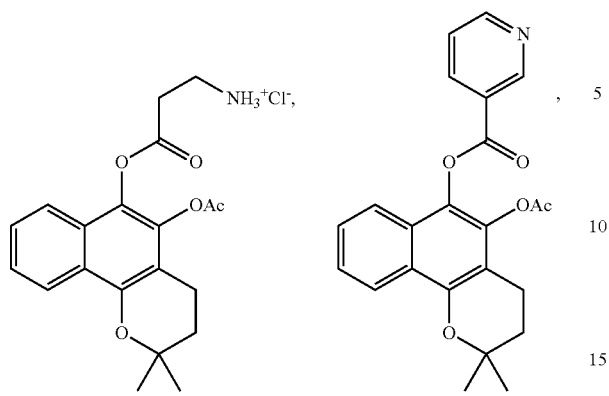
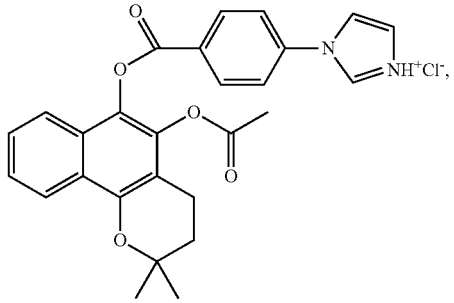
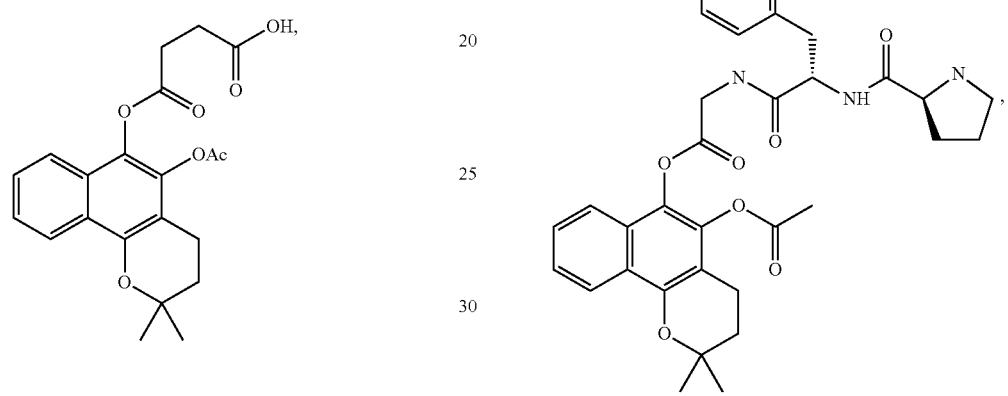
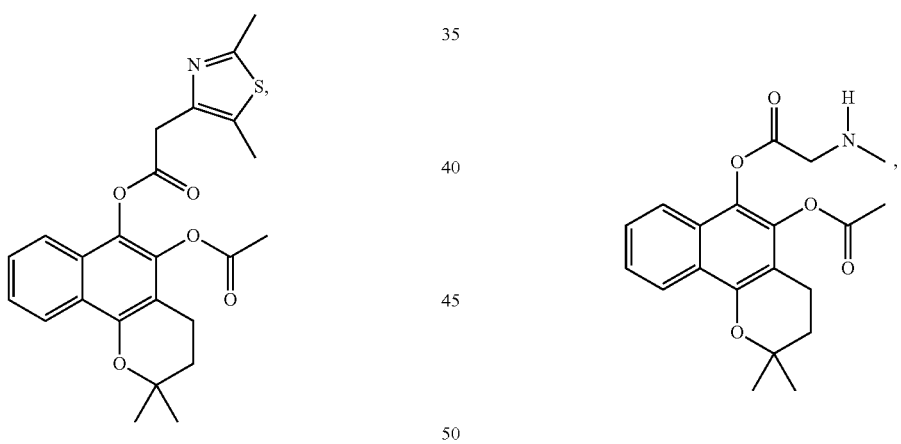
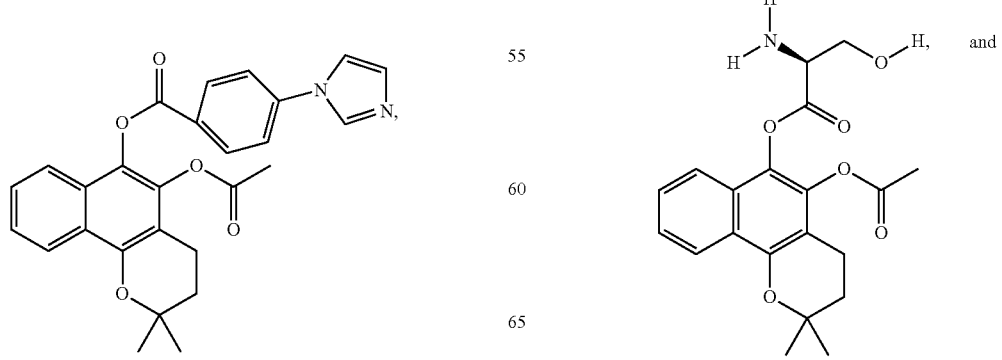

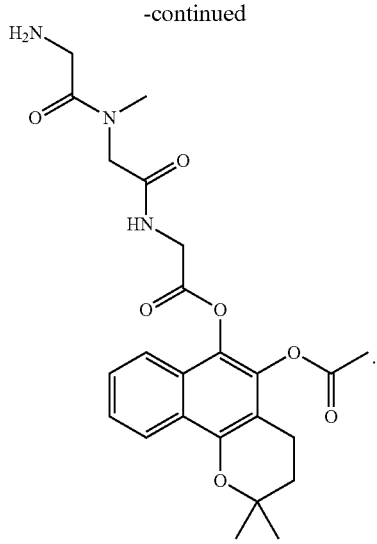

4. A pharmaceutical composition comprising a therapeutically effective amount of at least one quinone prodrug composition and a pharmaceutically acceptable excipient, wherein said quinone prodrug composition comprises a quinone compound of formula I

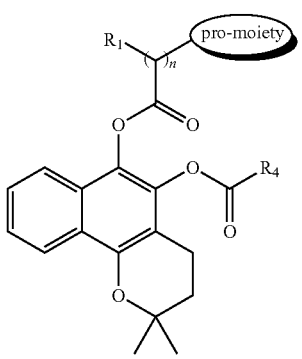

(I)

wherein
$R_1$ is H or $C_1$-$C_4$ alkyl, optionally substituted with a sulfyl (—SH or thio alkyl) group;
$R_4$ is $C_1$-$C_4$ alkyl, aryl or heteroaryl, wherein said aryl or heteroaryl is selected from the group consisting of phenyl, pyridyl, imidazole and thiazole, and is optionally substituted with one or more independently selected $C_1$-$C_3$ alkyl groups;
the pro-moiety is selected from —($C_1$-$C_{11}$)alkyl, —($C_0$-$C_6$)alkyl-aryl, —($C_0$-$C_6$)alkyl-heteroaryl, —($C_0$-$C_6$) alkyl-aryl-heteroaryl, —($C_0$-$C_6$)alkyl-COOH, —($C_1$-$C_6$)alkyl-OH, 1-pyridyl, 2-pyridyl, 3-pyridyl, 4-pyridyl, aryl-heteroaryl,

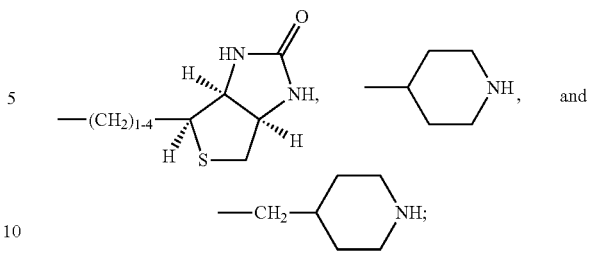

and
n is 0, 1, 2 or 3, with the proviso that when n is 0, $R_1$ is not present.

5. The pharmaceutical composition of claim 4, wherein the pharmaceutical composition is an aqueous solution.

6. The pharmaceutical composition of claim 4, wherein the pharmaceutical composition is a lyophilized solid.

7. The pharmaceutical composition of claim 4, wherein the pharmaceutical composition comprises 0.1 mg/ml to 10 mg/ml of the quinone prodrug composition.

8. The pharmaceutical composition of claim 4, further comprising a second anticancer agent.

9. The pharmaceutical composition of claim 8, wherein the second anticancer agent is selected from the group consisting of taxane derivatives, gemcitabine, cisplatin, imatnibmeasylate, and trastuzumab.

10. The pharmaceutical composition of claim 9, wherein the taxane derivative is paclitaxel or docetaxol.

11. A kit for the treatment of a mammalian cancer comprising at least one vial containing a quinone prodrug composition of claim 1.

12. A kit of claim 11, wherein the kit further comprises, within in the same vial or a separate vial, a second anticancer agent.

13. The kit of claim 12, wherein the second anticancer agent is selected from the group consisting of taxane derivatives, gemcitabine, cisplatin, imatnibmeasylate, and trastuzumab.

14. The kit of claim 13, wherein the taxane derivative is paclitaxel or docetaxol.

15. The quinone prodrug composition of claim 1, wherein $R_4$ is methyl.

16. The quinone prodrug composition of claim 1, wherein said aryl is phenyl.

17. The quinone prodrug composition of claim 1, wherein said aryl is substituted with $C_1$-$C_6$ alkyl.

18. The quinone prodrug composition of claim 1, wherein said heteroaryl is selected from the group consisting of pyridyl, imidazole and thiazole.

19. The quinone prodrug composition of claim 1, wherein said heteroaryl is substituted with $C_1$-$C_6$ alkyl.

20. The quinone prodrug composition of claim 1, wherein said pro-moiety is selected from —COOH, —$CH_2$—COOH and —($CH_2$)$_2$—COOH.

* * * * *